United States Patent
Venkatesh et al.

(10) Patent No.: US 10,441,554 B2
(45) Date of Patent: *Oct. 15, 2019

(54) ORAL AMPHETAMINE COMPOSITION

(71) Applicant: Adare Pharmaceuticals, Inc., Lawrenceville, NJ (US)

(72) Inventors: Gopi M. Venkatesh, Vandalia, OH (US); Michelle Schilling, New Carlisle, OH (US)

(73) Assignee: ADARE PHARMACEUTICALS, INC., Lawrenceville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,322

(22) Filed: Jun. 5, 2018

(65) Prior Publication Data

US 2018/0311187 A1 Nov. 1, 2018

Related U.S. Application Data

(63) Continuation of application No. 15/455,961, filed on Mar. 10, 2017.

(51) Int. Cl.
| | |
|---|---|
| *A61K 31/137* | (2006.01) |
| *A61K 9/50* | (2006.01) |
| *A61K 9/00* | (2006.01) |
| *A61K 9/20* | (2006.01) |
| *A61K 47/26* | (2006.01) |

(52) U.S. Cl.
CPC .......... *A61K 31/137* (2013.01); *A61K 9/0056* (2013.01); *A61K 9/2081* (2013.01); *A61K 9/2095* (2013.01); *A61K 9/5026* (2013.01); *A61K 9/5042* (2013.01); *A61K 9/5047* (2013.01); *A61K 9/5073* (2013.01); *A61K 9/5089* (2013.01); *A61K 47/26* (2013.01)

(58) Field of Classification Search
None
See application file for complete search history.

(56) References Cited

U.S. PATENT DOCUMENTS

| | | |
|---|---|---|
| 6,139,865 A | 10/2000 | Friend et al. |
| 7,919,115 B2 | 4/2011 | Venkatesh et al. |
| 8,077,288 B2 | 12/2011 | Kawashima |
| 8,545,881 B2 | 10/2013 | Venkatesh et al. |
| 8,709,491 B2 | 4/2014 | Tengler et al. |
| 9,572,781 B2 | 2/2017 | Venkatesh et al. |
| 2005/0232988 A1 | 10/2005 | Venkatesh et al. |
| 2006/0078614 A1 | 4/2006 | Venkatesh |
| 2009/0169620 A1 | 7/2009 | Venkatesh et al. |
| 2009/0202630 A1 | 8/2009 | Venkatesh et al. |
| 2011/0135724 A1 | 6/2011 | Venkatesh |
| 2011/0212171 A1 | 9/2011 | Venkatesh et al. |
| 2014/0322296 A1 | 10/2014 | Stollberg et al. |
| 2018/0256515 A1 | 9/2018 | Venkatesh et al. |

OTHER PUBLICATIONS

Evekeo® (amphetamine sulfate tablets, USP), Package insert/Prescribing/Labeling Information, Arbor Pharmaceuticals, LLC, AM-PI-08 1148D00 Rev. Sep. 2016, 2 pages.
"Evekeo (amphetamine sulfate tablets, USP) CII." USFDA Prescribing/Labeling Information. Arbor Pharmaceuticals, Inc. (Nov. 2015), 15 pages.
Childress, Ann C., et al., "The Efficacy and Safety of Evekeo, Racemic Amphetamine Sulfate, for Treatment of Attention-Deficit/Hyperactivity Disorder Symptoms: A Multicenter, Dose-Optimized, Double-Blind, Randomized, Placebo-Controlled Crossover Laboratory Classroom Study." Journal of Child and Adolescent Psychopharmacology (2015); 25 (5): 402-414.
Dahl, T.C., "Ethylcellulose" in Handbook of Pharmaceutical Excipients. Pharmaceutical Press and American Pharmacists Association 2009 (6th Edition) 262-267.
Sahoo, Susijit, et al., "Fast Dissolving Tablet: As a potential drug delivery system." Drug Invention Today (2010); 2 (2): 130-133.
Remington: The science and practice of pharmacy. 21st Edition (2005) pp. 899-900.
Drusano, G.L., "Pharmacokinetics/Pharmacodynamics in Drug Development." Remington: The Science of and Practice of Pharmacy, 21st Edition, Lippincott (2006); Chapter 63, pp. 1249-1257, 11 pages.
Venkatesh, G., "Granulation Approaches for Orally Disintegrating Formulations." Handbook of Pharmaceutical Granulation Technology, Third Edition, Informa Healthcare (2010); Parikh, D.M. (Ed.); Chapter 19, pp. 401-434, 36 pages.

*Primary Examiner* — Bethany P Barham
*Assistant Examiner* — Peter Anthopolos
(74) *Attorney, Agent, or Firm* — Cooley, LLP

(57) ABSTRACT

In various embodiments, the present invention is directed to oral pharmaceutical compositions. For example, in some embodiments, the present invention is directed to taste-masked compositions. In some embodiments, the taste masked compositions comprise a highly water soluble drug such as amphetamine, e.g., in the form of a salt such as amphetamine sulfate. In various embodiments, the present invention is directed to taste-masked, orally disintegrating compositions.

22 Claims, 7 Drawing Sheets

| Flavor Profile Definitions |
|---|
| Amplitude: Initial overall perception of the balance and fullness of a flavored product; considering the appropriateness of aromas and flavor notes present, their blend and intensity and existence of off-notes. |
| Amplitude Scale:  0    ½    1    1½    2    2½    3<br>          None    Low      Moderate    High |
| Character Notes: Aromatics, basic tastes, and feeling factors (listed in order of appearance along with a measurement of strength). |
| Intensity Scale:  0    ½    1    1½    2    2½    3<br>          None    Slight    Moderate    Strong |
| Aftertaste: Measurement of all sensation remaining at selected time intervals |

FIG. 10

ORAL AMPHETAMINE COMPOSITION

CROSS-REFERENCE TO RELATED APPLICATIONS

This application is a continuation of U.S. patent application Ser. No. 15/455,961, filed Mar. 10, 2017, which is hereby incorporated by reference in its entirety.

FIELD OF THE INVENTION

In various embodiments, the present invention is directed to oral pharmaceutical compositions. For example, in some embodiments, the present invention is directed to taste-masked compositions. In some embodiments, the taste masked compositions comprise a highly water soluble drug such as amphetamine, e.g., in the form of a salt such as amphetamine sulfate. In various embodiments, the present invention is directed to taste-masked, orally disintegrating compositions.

BACKGROUND OF THE INVENTION

Attention deficit-hyperactivity disorder (ADHD), among the most common disorders of childhood, is characterized by the inability to marshal and sustain attention, modulate activity level, and moderate impulsive actions. Difficulties are evident at home, where ADHD children often have a hard time following rules, often create disturbances at mealtime, bedtime, or on family outings, are in frequent conflict with siblings, and rarely complete homework without a struggle or in the absence of parental supervision. In the classroom, ADHD children often stand out because of their lack of concentration, failure to follow class routines, fidgetiness, inappropriate verbalizations and disruptiveness, and difficulty working independently. Such maladaptive behaviors are inconsistent with age and developmental level. Evidence of symptoms is obtained directly from the child, the parents and the teachers. The prevalence of ADHD is estimated at 3 to 7% of all children, and ADHD is a chronic condition with symptoms experienced over a lifetime.

Many drug therapies use immediate-release oral dosage forms administered at spaced intervals to provide and maintain a desired therapeutic effect over a prolonged therapy period.

For example, drugs used in treating Attention Deficit Disorder (ADD) and ADHD such as ADDERALL® and RITALIN® are administered two or three times a day. For various reasons, subjects often experience difficulty complying with this administration schedule. Conventional ADHD compositions such as ADDERALL® XR and METADATE® CD are only available in solid dosage forms for swallowing. Many people, especially children, have difficulty swallowing such standard solid dosage forms.

Amphetamines are non-catecholamine, sympathomimetic amines with CNS stimulant activity. Peripheral actions include elevations of systolic and diastolic blood pressures, and weak bronchodilator, and respiratory stimulant action. The racemic form of amphetamine in EVEKEO® differs from dextroamphetamine as in DEXEDRINE® or DEX-AMPEX or the mixed amphetamine salts in Adderall® as only 25% of the dose in EVEKEO® is in the form of the l-isomer. The l-isomer is more potent than the d-isomer in cardiovascular activity, but much less potent in causing CNS excitatory effects. The racemic mixture of EVEKEO® is also is less effective as an appetite suppressant when compared to dextroamphetamine.

EVEKEO® tablets containing racemic amphetamine sulfate, available in 5 and 10 mg dose strengths, are typically administered starting with the lowest dose, and the dosage may be individually adjusted for each patient. EVEKEO® is not recommended for children under 3 years of age. In children from 3 to 5 years of age, the initial dose is typically 2.5 mg daily; the daily dosage may be raised in increments of 2.5 mg at weekly intervals until the optimal response is obtained. In children 6 years of age or older, the starting dose is typically 5 mg once or twice daily; the daily dosage may be raised up to a maximum total daily dose of 40 mg in increments of 5 mg at weekly intervals until the optimal response is obtained. With tablets, the first dose is typically administered upon awakening, and additional doses (1 to 2) may be administered at intervals of 4 to 6 hours. Many pediatric patients experience difficulty in swallowing tablets and capsules, and many parents and care givers find it hard to ensure that young ADHD children swallowed their CNS stimulants without "cheeking". The availability of pleasant tasting orally disintegrating tablets which rapidly disintegrate on contact with saliva into a viscous, easy-to-swallow suspension would minimize, if not eliminate, these problems, and improve compliance.

U.S. Pat. No. 8,709,491 assigned to Neos Therapeutics is directed to easily ingested, once-daily oral compositions, including liquid drug suspensions, chewable compositions, and orally disintegrating compositions, which can be easily administered with or without water. These dosage forms, especially ODTs consist of two types of particles—uncoated resinate particles and resinate particles coated with a delayed or controlled release coating can provide an effective treatment over a prolonged period of time. However, ODT dosage forms favored by individuals who have difficulty swallowing conventional solid dosage forms (e.g., children or individuals with dysphagia), apart from being in the extended release form, contain a combination of 4 different salt forms with a dextro to levo isomer weight ratio of 3:1, and hence, are not substitutable for EVEKEO®.

SUMMARY OF THE INVENTION

In various embodiments, the present invention relates to orally disintegrating tablets (ODTs) that facilitate easy oral administration, for example to patients with Attention Deficit Hyperactivity Disorder (ADHD), especially young children, to provide rapid onset of action, i.e., to rapidly achieve effective control of ADHD symptoms. The ODT compositions of the present invention are easier to swallowing than conventional immediate release products (e.g., tablets or capsules). In particular embodiments, the present invention provides for pharmaceutical compositions which rapidly disintegrate on contact with saliva in the buccal cavity, thereby forming a smooth (non-gritty), easy-to-swallow, viscous suspension containing effectively taste-masked racemic amphetamine sulfate drug particles. Such compositions have superior taste characteristics compared to conventional pharmaceutical formulations, particularly those in which the bitter tasting drug is not coated or taste-masked. The compositions of the present invention provide an escalating in vivo plasma concentration profile of amphetamine sulfate after administration.

One aim of the invention is therefore to remedy the disadvantages of conventional formulations and to provide an easily ingested, orally disintegrating tablet dosage form, having a pleasant texture (smooth, non-gritty mouthfeel), upon rapid disintegration on contact with saliva in the oral cavity, and having no aftertaste following swallowing of viscous suspension containing well taste-masked drug particles to provide a plasma concentration profile similar to that of, and/or being bioequivalent to, RLD EVEKEO®.

BRIEF DESCRIPTION OF THE FIGURES

FIG. 10 shows the "Flavor Profile Method" used in the open-label comparative sensory organoleptic taste assessment of 30 mg Amphetamine Sulfate IR ODT (Beads) vs. 30 mg Amphetamine Sulfate IR ODT (Microcaps).

DETAILED DESCRIPTION OF THE INVENTION

Figure 1:
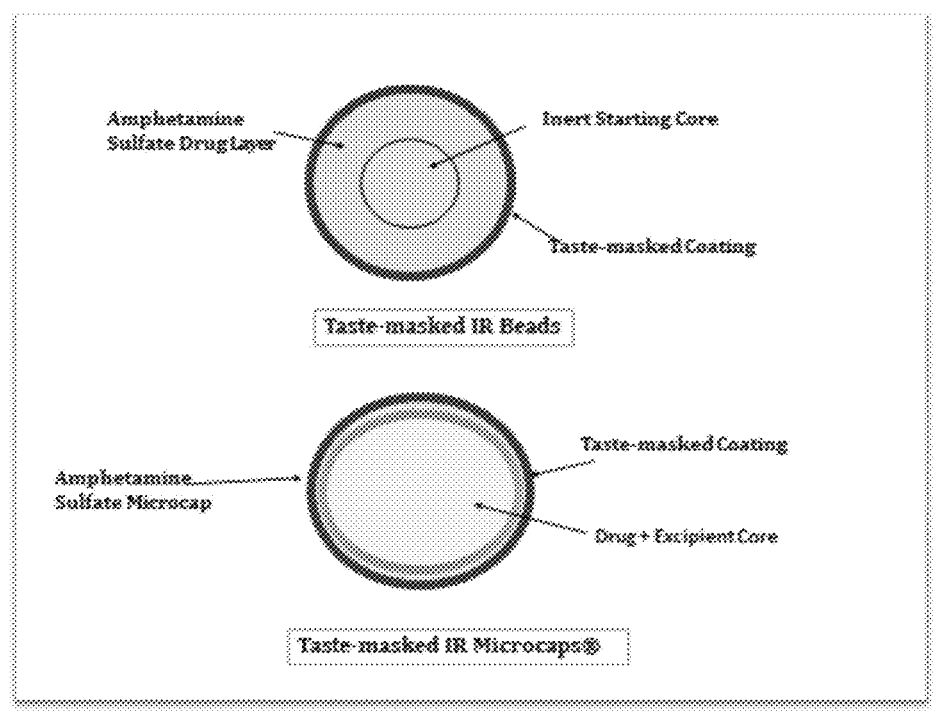
FIG. 1 shows schematically the construct of taste-masked racemic amphetamine sulfate microparticles [IR Beads (top) and Microcaps® (bottom)].

Throughout the present document, all expressions of percentage, ratio, and the like, will be in weight units unless otherwise indicated.

The term "drug", "active" or "active pharmaceutical ingredient" as used herein includes a pharmaceutically acceptable and therapeutically effective compound (e.g., amphetamine), pharmaceutically acceptable salts, stereoisomers and mixtures of stereoisomers, solvates (including hydrates and/or acid addition salts, such as amphetamine sulfate), and/or esters thereof (e.g., of amphetamine).

The particle size distributions, d(0.1), d(0.5) and d(0.9) are defined in terms of the mean particle size, respectively of 10%, 50% and 90% of the particles as determined by a laser diffraction spectrophotometer.

As used herein, the term "pharmaceutically effective" refers to that amount of amphetamine sulfate, which diminishes one or more symptoms of the disease or disorder being treated, viz., Attention Deficit Hyperactivity Disorder (ADHD). For example, a pharmaceutically effective amount for the treatment of ADHD refers to the amount which when administered diminishes one or more symptoms of ADHD, such as lack of concentration, failure to follow class routines, fidgetiness, inappropriate verbalizations and disruptiveness. The precise therapeutic dosage of racemic amphetamine sulfate necessary to be pharmaceutically effective will vary with age, size, sex and condition of the subject, the nature and severity of the disorder or disease to be treated, and the like; thus, a precise pharmaceutically effective amount cannot be specified in advance and in the present case, has been determined by the innovator of the reference listed drug (RLD).

The term "orally disintegrating tablet" (ODT) as used herein is intended to encompass any compressed pharmaceutical dosage formulations of all shapes and sizes, which rapidly disintegrate on contact with saliva in the oral cavity into a viscous smooth (non-gritty), easy-to-swallow suspension, although it can be ingested with water if the patient so desires.

The term "about", as used herein to refer to a numerical quantity, includes "exactly". For example, "about 60 seconds" includes 60 seconds, exactly, as well as values close to 60 seconds (e.g., 50 seconds, 55 seconds, 59 seconds, 61 seconds, 65 seconds, 70 seconds, etc.). In some instances, the term "about" in the context of the disclosure refers to an approximate amount distinct from adjacent values. For example, in a disclosure of "about 65, about 70, about 75," "about 70" refers to an amount as low as a value greater than 65.5 or less than 72.5. When the term "about" is used in reference to a range of values, the term "about" refers to both the minimum and maximum value of the range (e.g., "about 1-50 μm" means "about 1 μm to about 50 μm").

An orally disintegrating tablet formulation typically will have most of the following attributes/properties:
 drug particles should be effectively taste-masked such that drug dissolution in saliva in the oral cavity, as well as after taste, can be avoided;
 taste-masked drug particles may have a desired particle size range; for example, the maximum particle size of less than 500 μm, for example with a d(0.9) of less than 300 μm (i.e., 90% of taste-masked drug particles are smaller than 300 μm); otherwise, subjects taking the orally disintegrating tablet experience gritty mouthfeel;
 drug dissolution from the ODTs is ideally similar to that of the reference listed drug (RLD) so that an expensive regulatory pathway for product approval can be avoided;
 tablet formulation should comprise soluble excipients forming a viscous smooth, easy-to-swallow suspension containing effectively taste-masked drug particles upon disintegration of the ODT on contact with saliva in the buccal cavity.

The drug particles are taste-masked using one of several conventional methods. For example, drug particles are taste-masked by solvent coacervation wherein drug particles are suspended in a solution/suspension of ethylcellulose (having a viscosity of 100 cps), or ethyl cellulose in combination with a gastrosoluble pore-former such as calcium carbonate, in cyclohexane at approximately 80° C. and subjected to controlled cooling to cause effective encapsulation of drug particles by phase-separating ethylcellulose or ethylcellulose-calcium carbonate. Alternatively, drug particles can be taste-masked by spray coating drug microparticles with a solution of a pharmaceutically acceptable water insoluble polymer such as ethylcellulose, alone or in combination with a pharmaceutically acceptable gastrosoluble pore-former, such as calcium carbonate or Amino Methacrylate Copolymer commercially known as EUDRAGIT® EPO or E100 in a fluid-bed coater.

Suitable pharmaceutically acceptable water insoluble polymers include, without limitation, ethylcellulose, cellulose acetate, cellulose acetate butyrate, polyvinyl acetate, neutral acrylate-methacrylate copolymers (Eudragit RL, RS, NE30D), etc. Suitable gastrosoluble polymers include aminoalkyl methacrylate copolymer (Eudragit EPO), polyvinylacetal diethylaminoacetate (AEA), etc.

Racemic amphetamine sulfate is freely water soluble and highly bitter. However, drug particles taste-masked by either of the taste-masking methods discussed above have been evaluated and do not possess an acceptable particle size distribution, organoleptic properties, and dissolution properties that are bioequivalent to the RLD (i.e., EVEKEO®) in a bioavailability study in humans and promote adherence to dosing regimens. After extensive investigations, the present inventors discovered that agglomerating a homogeneous blend of mannitol and racemic amphetamine sulfate by solvent coacervation with ethylcellulose [e.g., ethylcellulose with a viscosity of 100 cps (EC-100)] followed by fluid-bed coating with ethylcellulose [e.g., ethylcellulose with a viscosity of 10 cps (EC-10)] in combination with a gastrosoluble pore-forming polymer, EUDRAGIT® EPO or E100 provides acceptable organoleptic properties and bioequivalence to EVEKEO®. Without being bound by theoretical arguments, the EPO polymer in the EC-10/EPO coating is insoluble/impermeable to saliva in the oral cavity and hence, the EC-10/EPO membrane coating remains intact even after contact with saliva such that the bitter amphetamine sulfate in the coated microparticle does not dissolve and consequently, the subject wouldn't experience a bitter drug taste. The EPO polymer in the same EC-10/EPO coating rapidly dissolves on contact with an acidic buffer or upon entry into the stomach, thereby not having any effect on the drug release from the coacervated drug-microparticles and/or being bioequivalent to RLD EVEKEO®. If the taste-masked microparticles are sufficiently small (e.g., having a d(0.9) of less than 300 μm—i.e., 90% of taste-masked drug particles are smaller than 300 μm), subjects taking the coated microparticles or an orally disintegrating tablet containing such coated microparticles avoid experiencing a gritty mouthfeel.

The rate of dissolution of the amphetamine sulfate in the ODT compositions of the present invention were evaluated using the United States Pharmacopoeia Apparatus 2 (paddles @ 50 rpm in 900 mL of 0.01N HCl buffer). When using the United States Pharmacopoeia Apparatus 2 test, the rate of dissolution of the drug (e.g., amphetamine sulfate) was comparable to that of conventional, non-ODT compositions, for example about 70% or more, about 75% or more, about 80% or more, about 85% or more, about 90% or more, about 95% or more, or about 100% of the total amount of amphetamine sulfate was released in 30 minutes.

The term "substantially disintegrates" means a level of disintegration amounting to disintegration of at least about 50%, at least about 60%, at least about 70%, at least about 80%, at least about 90%, or about 100% disintegration of the ODT composition.

The terms, "substantially the same", mean that the amphetamine release profile of the ODT compositions of the present invention (as defined) is similar to (e.g., bioequivalent as defined by US FDA guidelines) the amphetamine release profile of non-ODT EVEKEO®. Alternatively, the terms "substantially the same" mean an amphetamine release profile which is statistically indistinguishable from (e.g., bioequivalent as defined by US FDA guidelines) the amphetamine release profile of non-ODT immediate release oral amphetamine composition having the same dose.

The orally disintegrating compositions of the present invention can comprise any suitable dose of amphetamine, or a pharmaceutically acceptable salt thereof. For example, the dose can be about 5 mg to about 40 mg, including about 5 mg, about 10 mg, about 15 mg, about 20 mg, about 25 mg, about 30 mg, or about 40 mg. The dose is expressed as the equivalent weight of the free base form of amphetamine, unless otherwise indicated. In particular embodiments, the dose is about 5 mg or about 10 mg.

The form of amphetamine can be any suitable form, for example, D- or L-amphetamine, racemic amphetamine, and including the free base or salts of amphetamine such as the sulfate salt thereof. Other salts known in the art (e.g., acid addition salts such as the hydrochloride, hydrobromide, aspartate, phosphate, succinate, saccharate, etc.) can also be used.

Unless indicated otherwise, all percentages and ratios are calculated by weight. Unless indicated otherwise, all percentages and ratios are calculated based on the total composition.

A multiparticulate composition of the present invention, in the form of an ODT comprises core particles (crystals or granules, beads or pellets comprising bitter-tasting racemic amphetamine sulfate) that are taste-masked first by solvent coacervation, i.e., encapsulated with water-insoluble ethylcellulose (first membrane) and secondly by fluid-bed coating with a mixture of a water-insoluble polymer and a gastrosoluble polymer (second membrane).

In most embodiments, the ODT compositions of the present invention comprise a therapeutically effective amount of amphetamine sulfate racemate coated with one, or in many embodiments, two taste-masking layers, e.g. in the form of a tablet further comprising disintegrant-containing rapidly dispersing granules. Upon administration of an ODT tablet of the present invention to the oral cavity of a patient, the tablet disintegrates rapidly in the patient's oral cavity into taste-masked, amphetamine sulfate containing particles while the sugar alcohol/saccharide containing granules rapidly dissolve to form a smooth suspension that can be readily swallowed.

One embodiment of the invention is therefore an orally disintegrating tablet, a solid dosage form characterized in that:
  it comprises at least two types of granules—one population of taste-masked racemic amphetamine sulfate containing microparticles and another population of rapidly dispersing microgranules consisting of a sugar alcohol, a saccharide or a mixture thereof together with a disintegrant—blended with other excipients and compressed at low compression forces into ODTs;
  it rapidly disintegrates on contact with saliva in the oral cavity into a viscous, smooth (non-gritty), easy-to-swallow suspension swallowed without experiencing aftertaste;
  it dissolves sufficiently rapid to be bioequivalent to the RLD, EVEKEO® (IR amphetamine sulfate tablets).

In various embodiments, the ODT compositions of the present invention are bioequivalent to EVEKEO® (IR amphetamine sulfate tablets). For example, the ODT compositions of the present invention have PK parameters within about 80-125% of one or more of the mean $AUC_{inf}$, $C_{max}$ or $T_{max}$ of EVEKEO® of equivalent dose strength. For example, the $AUC_{0\text{-}inf}$ of the ODT compositions of the present invention range from about 80% to about 125% of about 400-600 hr*ng/mL (80-125% of about 400 hr*ng/mL to about 80-125% of about 600 hr*ng/mL), including 80-125% of: about 400, about 410, about 420, about 430, about 440, about 450, about 460, about 470, about 480, about 490, about 500, about 510, about 520, about 530, about 540, about 550, about 560, about 570, about 580, about 590, or about 600 hr*ng/mL. For example, the $C_{max}$ of the ODT compositions of the present invention range from about 80-125% of about 25-35 ng/mL, including 80-125% of: about 25, about 26, about 27, about 28, about 29, about 30, about 31, about 32, about 33, about 34, or about 35 ng/mL. For example, the $T_{max}$ of the ODT compositions of the present invention range from about 80-125% of about 2-4 hrs, including 80-125% of: about 2 hr, 2.1 hr, 2.2 hr, 2.3 hr, about 2.4 hr, about 2.5 hr, about 2.6 hr, about 2.7 hr, about 2.8 hr, about 2.9 hr, about 3 hr, about 3.1 hr, about 3.2 hr, about 3.3 hr, about 3.4 hr, about 3.5 hr, about 3.6 hr, about 3.7 hr, about 3.8 hr, about 3.9 hr, or about 4 hr.

In accordance with one aspect of the invention, the present invention is directed to a taste-masked multiparticulate pharmaceutical composition comprising:
(a) a drug-containing core particle (crystal, granule, pellet, bead and the like);
(b) a first taste-masking membrane on said drug-containing core particle comprising a water-insoluble polymer applied by solvent coacervation;
(c) a second taste-masking membrane on said coacervated drug-containing core particle comprising a combination of a water-insoluble polymer and a gastrosoluble polymer at a ratio ranging from about 95/5 to about 50/50 having a thickness of from about 5% to about 50% based on the weight of the coated particle and an average particle size of not more than about 400 μm, thereby avoiding gritty mouthfeel, is disclosed.

The orally disintegrating pharmaceutical composition of the invention has an average patient perceptible intensity of bitterness of less than 1 minute when the orally disintegrating composition having a dose equivalent to 30 mg of racemic amphetamine sulfate is evaluated by the sensory panel using the flavor profile method. In accordance with certain embodiments, the composition exhibits acceptable taste-masking when the composition is placed in the oral cavity for 3 minutes, or in various embodiments for 2 minutes, or for 60 seconds, or in particular embodiments until it is swallowed leaving little or no aftertaste (i.e., experiencing no gritty or chalky taste) and the composition provides rapid, substantially-complete release of the dose upon entry into the stomach, i.e., releases not less than 90% of the dose in 30 min when tested for dissolution using United States Pharmacopoeia Apparatus 1 (Paddles@ 50 rpm in 900 mL of pH 1.2 buffer).

A taste-masked multiparticulate pharmaceutical composition in the ODT (orally disintegrating tablet) form, which disintegrates on contact with saliva in the buccal cavity in about 60 seconds forming a smooth easy-to-swallow suspension (no gritty or chalky aftertaste) is also disclosed. The ODT may comprise the drug-containing core particle (crystal, granule, pellet, bead and the like), with a second taste-masking membrane on the drug-containing core particle. The second taste-masking membrane may comprise a water-insoluble polymer and a gastrosoluble polymer at a ratio ranging from about 95/5 to about 50/50 (e.g., about 95/5, about 90/10, about 85/15, about 80/20, about 75/25, about 70/30, about 65/35, about 60/40, about 55/45, or about 50/50, including all ranges therebetween) having a thickness of from about 5% to about 50% (e.g., about 5%, about 10%, about 15%, about 20%, about 25%, about 30%, about 35%, about 40%, about 45%, or about 50%, including all ranges therebetween) based on the weight of the coated microparticle with an average particle size of not more than about 400 μm, or in some embodiments not more than 300 μm. The ODT may also include a rapidly-dispersing microgranule with an average particle size of not more than about 300 μm, or in some embodiments not more than 200 μm, comprising a disintegrant and a sugar alcohol or a saccharide or a combination thereof, each having an average particle diameter of not more than about 30 μm, and optionally pharmaceutically acceptable excipients typically used in ODT formulations, viz., flavors, a sweetener, coloring agents, and a disintegrant.

In accordance with particular embodiments, the method of preparing a taste-masked multiparticulate composition includes layering amphetamine sulfate from a polymeric binder solution onto an inert particle selected from the group consisting of sugar spheres and cellulose spheres. Fluid bed or pan coating may be used to apply the active and polymeric binder solution.

In accordance with certain embodiments, the drug-containing particle is a microgranule or an extruded/spheronized pellet comprising one or more pharmaceutically acceptable active ingredient(s), a polymeric binder, which imparts resilient characteristics to dried microgranules, a hydrophilic filler/diluent, and optionally a flavor, a sweetener and/or a disintegrant.

The water-insoluble polymer (e.g., ethylcellulose with an average viscosity of 10 cps) and the gastrosoluble polymer (e.g., Eudragit EPO) may be present at a weight ratio of from about 95/5 to 50/50, more particularly from about 85/15 to 65/35, and the membrane thickness varying from about 5% to 50%, more particularly from about 10% to 30%, by weight in accordance with particular embodiments.

In accordance with some particularly useful embodiments, the taste-masked multiparticulate pharmaceutical composition includes rapidly-dispersing microgranules comprising a disintegrant, for example crospovidone, and a sugar alcohol (for example mannitol) or a saccharide (lactose) or a combination thereof, each having an average particle diameter of not more than about 30 μm and a ratio of sugar alcohol and/or saccharide to disintegrant varying from about 90/10 to about 99/1

The rapidly-dispersing microgranules and taste-masked microparticles may be present in the ratio of about 6/1 to 2/1, more particularly from about 4/1 to 3/1, to achieve a smooth mouthfeel in some embodiments of the taste-masked composition.

A method of manufacturing a taste-masked multiparticulate composition of racemic amphetamine sulfate is also provided. The method may comprise the steps of:
a) preparing core particles of racemic amphetamine sulfate as microcapsules by coacervation process, as granules by a conventional granulation process, as beads by drug-layering onto inert particles from a polymeric binder solution in a fluid-bed equipment, as microgranules, or as pellets by a conventional granulation of amphetamine sulfate, one or more polymeric binder(s), a hydrophilic filler/diluent, and optionally a flavor, a sweetener, and/or a disintegrant or granulation-extrusion-spheronization process; and
b) coating core particles by applying a membrane comprising a mixture (at a ratio of 95/5 to 50/50) of water-insoluble ethylcellulose and gastrosoluble Eudragit E100 dissolved in a mixture of acetone and purified water, the membrane coating comprising approximately from about 5% to about 30% based on the total weight of the coated particles.

In a particular embodiment of the invention, the method comprises the steps of:
a) preparing drug containing core particles (crystals with a particle size distribution of 20-500 µm, more particularly from about 50-300 µm, beads, microgranules, pellets) of racemic amphetamine sulfate as described above;
b) taste-masking core particles by applying a membrane comprising a mixture of water-insoluble and gastrosoluble polymers as described above, the membrane coating comprising approximately from about 5% to about 50% based on the total weight of the coated particles;
c) granulating a disintegrant such as crospovidone with a sugar alcohol or a saccharide, or a combination thereof, each having an average particle diameter of not more than 30 µm, with water or an alcohol-water mixture in a conventional granulator and drying in a fluid bed equipment to produce granules with an average particle size not more than 400 µm (more particularly not more than 300 µm);
d) blending taste-masked microparticles of step (b) with rapidly disintegrating microgranules of step (c) and other optionally acceptable ingredients such as a flavoring agent, a coloring agent, a sweetener and additional disintegrant in sufficient quantities; and
e) compressing the mixture of step (d) into tablets using a conventional rotary tablet press equipped with an external lubrication system to pre-lubricate the dies and punches.

Useful polymeric binders include, without limitation, polyvinylpyrrolidone (PVP), polyethylene oxide, hydroxypropyl methylcellulose (HPMC), hydroxypropylcellulose (Klucel® LF from Aqualon) and mixture thereof.

The water-insoluble polymer (e.g., ethylcellulose with an average viscosity of 100 cps for use in solvent coacervation or an average viscosity of 10 cps for use in fluid-bed coating solvent) and the gastrosoluble polymer (e.g., EUDRAGIT EPO) may be present at a weight ratio of from about 95/5 to 50/50, more particularly from about 85/15 to 55/45, and the membrane thickness varying from about 5% to 50%, more particularly from about 10% to 30%, by weight in accordance with particular embodiments.

The water-insoluble polymers suitable for taste-masking of bitter drugs by coating in fluid-bed equipment include, but are not limited to, ethylcellulose, cellulose acetate, cellulose acetate butyrate, methacrylate copolymers available under the trade name of EUDRAGIT® (type RL, RS and NE30D). The gastrosoluble polymers include, but are not limited to maltrin, an aminoalkyl methacrylate copolymer available under the trade name of EUDRAGIT® (type E100 or EPO), polyvinylacetal diethylaminoacetate e.g., AEA® available from Sankyo Company Limited, Tokyo (Japan), and the like.

Representative examples of plasticizers that may be used to plasticize the membranes include triacetin, tributyl citrate, triethyl citrate, acetyl tri-n-butyl citrate, polyethylene glycol, polypropylene glycol, diethyl phthalate and mixture thereof.

The ODT compositions described herein typically include rapidly-dispersing microgranules. One or more sugar alcohols and/or saccharides and a disintegrant are granulated in a high-shear granulator and dried in fluid bed equipment to produce rapidly-dispersing microgranules. Rapidly-dispersing microgranules typically will contain sugar alcohol and/or saccharide and disintegrant at a ratio varying from about 90/10 to about 99/1, or in some embodiments from about 90/10 to about 95/5 by weight (sugar alcohol and/or saccharide to disintegrant). The sugar alcohol may be selected from the group consisting of mannitol, sorbitol, xylitol, maltitol and the like while the saccharide may be selected from the group consisting of lactose, sucrose, maltose or as a mixture of two or more, each of which is characterized by an average particle size of not more than about 30 µm. A disintegrant or a so-called super-disintegrant may be selected from the group consisting of crospovidone (cross-linked PVP), sodium starch glycolate, crosslinked sodium carboxymethyl cellulose, and low substituted hydroxypropylcellulose.

In another embodiment, a method of manufacturing orally disintegrating tablets of the present invention comprises the following steps:
(a) preparing crystalline amphetamine sulfate, amphetamine sulfate layered beads, or amphetamine sulfate-containing microgranules by granulating crystalline amphetamine sulfate and one or more diluents/fillers such as lactose, mannitol, microcrystalline cellulose and mixtures thereof;
(b) preparing taste-masked Microcaps® by microencapsulation with ethylcellulose or fluid-bed coating with ethylcellulose
(c) granulating one or more sugar alcohols and/or saccharides, each having an average particle diameter of not more than about 30 µm, with a disintegrant such as crospovidone, using water or an alcohol-water mixture in a conventional granulator, and drying the granulate in fluid-bed equipment or a conventional oven to produce rapidly-dispersing microgranules with an average particle size of not more than about 400 µm, as described in U.S. patent application Ser. No. 10/827,106, filed Apr. 19, 2004;
(d) blending the microgranules of step (a) with one or more flavoring agents, a sweetener, microcrystalline cellulose, additional disintegrant, and the rapidly-dispersing microgranules of step (b); and
(d) compressing the blend of step (c) into tablets using e.g. a conventional rotary tablet press equipped with an external lubrication system to pre-lubricate the dies and punches.

One objective of the present invention was to develop a stable tablet formulation that would disintegrate in the oral cavity over a relatively short time period and was therefore designed to have a pleasant taste and mouth-feel, with a minimal perception of grittiness in the oral cavity during disintegration. Effective taste-masking of the active was achieved through microencapsulation and secondary application of a polymer coating in a fluid-bed coater. A sweetener and an acidulant were included to further aid in taste-masking the bitter amphetamine drug and enhance the overall taste of the tablet. Finally, the formulation was designed to be easily manufactured and scaled-up using common pharmaceutical excipients, with a robust manufacturing process. The correct dose for each strength is achieved by adjusting the quantities of the drug product intermediate (based on assay) and mannitol USP within the blend in equal, but opposite, amounts to maintain the desired total quantity of the two components in the formulation.

The compositions of the present invention are suitable for treating conditions treatable with, e.g., an amphetamine, for example racemic amphetamine (including pharmaceutically acceptable salts thereof), particularly racemic amphetamine sulfate. Such conditions include narcolepsy, attention deficit disorder with hyperactivity, and exogenous obesity.

It is to be understood that while the invention has been described in conjunction with the particular specific embodiments thereof, that the description above as well as the examples that follow are intended to illustrate and not limit the scope of the invention. Any modification within the scope of the invention will be apparent to those skilled in the art to which the invention pertains.

Example 1

Amphetamine Sulfate IR Beads (Drug Load: 30%; Batch Size: 4000 g) in Glatt GPCG 5

Purified water (12,860.5 g) was added to a suitable stainless steel container and then the amphetamine sulfate (1200.0 g) was slowly added to dissolve while mixing with a low shear agitator for not less than (NLT) 10 minutes (until visually dissolved). The povidone (150.0 g) was added to the solution and mixed for NLT 15 minutes until dissolved. The OPADRY CLEAR (80.0 g) was added to purified water (1374.5. g) in a stainless steel container and mixed using a low shear agitator for NLT 60 minutes.

The microcrystalline cellulose (MCC) Celphere (CP-102: 2570.0 g) was loaded into the pre-heated fluid-bed coater, Glatt GPCG-5 and airflow was adjusted to achieve adequate fluidization (see preheating parameters below). The IR coating solution was sprayed while adjusting inlet temperature and airflow to achieve target bed temperature (see coating parameters below). After 10-20 min, gradually increased the spray rate while adjusting flow parameters to maintain the target bed temperature. After the entire IR coating solution was sprayed, the seal coating solution was sprayed on to drug layered beads and the seal coated beads were dried for 5 minutes. Then the IR beads were discharged and sieved through US 50-120 mesh sieves.

Procedures for Fluid-Bed Coating with EUDRAGIT EPO at 30% Coating (Formula B)

EUDRAGIT EPO (252 g) was slowly combined with the Acetone USP (3078 g) in a stainless steel container and mixed using a low shear agitator until a clear solution was obtained. Purified Water (162 g) was added to the solution and dibutyl sebacate (18 g) added to dissolve while mixing. Finally magnesium stearate (90 g) was added to the solution for homogeneously disperse in the solution while mixing. Moderate agitation was maintained throughout spraying.

Procedures for Fluid-bed Coating with EC-10/EPO (Formula A)

EUDRAGIT EPO (112 g) was slowly combined with the Acetone USP (2268 g) in a stainless steel container and mixed using a low shear agitator until a clear solution was obtained. The ethylcellulose (112.0 g) was slowly added and mixing was continued until a clear solution was obtained. The purified water USP was added to the solution and followed by adding the dibutyl sebecate NF and continuing the mixing for 15 minutes. The magnesium stearate NF was added to homogeneously disperse in the solution mixing continued throughout spray.

The IR beads were loaded into the pre-heated fluid-bed coater, Glatt GPCG-3 (bottom spray (7" in diameter) Wurster insert; 18 mm partition height; 14 mm tubing; 100 mesh screen; Distribution plate: C; Atomization air pressure: 1.5 bar, and nozzle tip size: 1 mm; see preheating parameters—Inlet air temp: 35° C.; Air flow: 16 cfm; Dew point: 2° C.) and coated by spraying the coating solution under the following process parameters (Inlet air temp: 45° C.; Air flow: 16 cfm; Spray rate: 6-12 ml/mL; Target bed temp:

TABLE 1

Set-up of Fluid-bed Coater (Glatt GPCG 5 with Accessories and Process Parameters)

Batch Date:
Atomization Air Pressure (bar): 1.5
Distribution Plate: B
Machine: Glatt GPCG-5 9" diameter Wurster, 15 mm partition, 16 mm tubing, 200 mesh screen, dedicated Filter Bag Nozzle Height: Flush with air cap
Nozzle Tip Size: 1.0 mm
Filter Shake Interval/Duration: 30 sec/5 sec

| Preconditioning Parameters: | DL Coating Parameters: | Seal Coating Parameters: |
| --- | --- | --- |
| Inlet Air Temp.: 70° C. | Inlet Air Temp.: 65 to 79° C. | Inlet Air Temp.: 65° C. |
| Air Flow CV %: 25% (80 cfm) | Air Flow: 19% to 23.5% (~20 cfm) | Air Flow: 20 cfm |
| Dewpoint: 2° C. | Initial Spray Rate: 14 to 21 ml/min | Spray Rate: 8 ml/min |
| | Target Bed Temp: 42-44° C. | Targ Bed Temp: 42-44° C. |

Amphetamine Sulfate IR Beads (Drug Load: 24%; Batch Size: 1250 g) in Glatt GPCG 3

The IR coating solution was prepared by dissolving amphetamine sulfate (300 g) and povidone (37.5 g) in Purified Water (3215.1 g) as described above. The microcrystalline cellulose (MCC) Celphere (CP-102: 887.5 g) was loaded into a pre-heated fluid-bed coater, Glatt GPCG-3 (bottom spray (7" in diameter) Wurster insert; 18 mm partition height; 14 mm tubing; 100 mesh screen; Distribution plate: C; Atomization air pressure: 1.5 bar; Nozzle tip size: 1 mm) and coated by spraying the IR coating solution under the following process parameters (Inlet air: 48° C.; Air flow: 16 cfm, initial Spray rate: 6 mL/min and target Product temperature: 42-44° C. in order to achieve adequate fluidization and maintain product temperature) as described above. After 10-20 min, the spray rate was gradually increased to complete drug layering. Following seal coating, IR beads were dried for 5 mins, discharged and sieved to discard oversized (>50 mesh) and under sized (<120 mesh) particles.

29-31° C.). After 10-20 mins, the spray rate was gradually increased to 12 ml/mL to complete coating. Following coating, the taste-masked beads were dried for 5 mins, discharged and sieved to discard oversized (>60 mesh) and under sized (<120 mesh) particles.

The IR beads (840 g) prepared in GPCG 3 at a drug load of 24% by weight were loaded into the pre-heated fluid-bed coater, Glatt GPCG-3 (bottom spray (7" in diameter) Wurster insert; 18 mm partition height; 14 mm tubing; 100 mesh screen; Distribution plate: C; Atomization air pressure: 1.5 bar, and nozzle tip size: 1 mm; see preheating parameters—Inlet air temp: 35° C.; Air flow: 16 cfm; Dew point: 2° C.) and coated by spraying the IR coating solution under the following process parameters (Inlet air temp: 35-40° C.; Air flow: 16 cfm; Spray rate: 6-12 ml/mL; Target bed temp: 27-30° C.). After 10-20 mins, the spray rate was gradually increased to 12 ml/mL to complete coating. Following coating, the taste-masked beads were dried for 5 mins, discharged and sieved to discard oversized (>50 mesh) and under sized (<120 mesh) particles.

Manufacture of Rapidly-Dispersing Microgranules:

The rapidly-dispersible microgranules comprising a sugar alcohol such as mannitol and a disintegrant such as crospovidone were manufactured following the procedures disclosed in U.S. Pat. Nos. 8,077,288 and 8,545,881, both of which were herein incorporated in their entirety for all purposes. In most of the embodiments of the present invention, D-mannitol (152 kg) with an average particle size of approximately 20 μm or less (Pearlitol 25 from Roquette, France) was blended with 8 kg of cross-linked povidone (Crospovidone XL-10 from ISP) in a high shear granulator (GMX 600 from Vector) and granulated with purified water. The high shear granulation was passed through a Comil from Quadro, dried in a fluid-bed dryer, and again passed through the Comil to mill oversized granules. The rapidly-dispersible microgranules thus obtained typically had an average particle size in the range of approximately 125-200 μm.

Amphetamine Sulfate 30 mg IR ODT (Beads or Microcaps®)

Amphetamine Sulfate 30 mg IR ODT (Beads) or Amphetamine Sulfate 30 mg IR ODT (Microcaps®), a directly compressible orally disintegrating tablet, was designed to deliver an accurate dose of amphetamine sulfate to the target site of action in a convenient and palatable dosage form, with favorable organoleptic properties, such as mouth-feel and after-taste. The drug product functions by rapidly disintegrating in the oral cavity after administration, without the need for water. The drug product is comprised of amphetamine sulfate and other common pharmaceutical excipients used in the manufacture of ODTs. The quantitative unit dose composition for Amphetamine Sulfate 30 mg IR ODT (Beads) is provided in Table 2.

One half of the rapidly dispersing granules (796.8 g) of was added to a 3 L Bin Blender, followed by the IR Beads (168.0 g), Silicified PROSOLV SMCC 90, Microcrystalline Cellulose NF (120.0 g), Crospovidone (60.0 g), citric acid (15.6 g) and malic acid (8.4 g), sucralose (7.2 g) and the remaining rapidly dispersing granules to the bin blender and blended for 20 minutes at 20 rpm. The Sodium Stearyl Fumarate (24.0 g) was then added and blended an additional 5 minutes at 20 rpm. The blend was transferred from the bin blender into a tared and labeled bag.

The Fette 52i was set up for 8 Station operation (½ tooled) utilizing a power feed frame, 1" mono cams and a 10 mm fill cam. The hopper was charged with the blend of Formula ODT A (see Table 2 for details). Adjusted fill depth to achieve tablet weight of 550 mg. Both pre-compression and main compression forces were adjusted to achieve tablets with an average crushing strength of 45 N. Once achieved, the tablet press was operated in 'auto' mode and NLT 45 tablets were collected for testing for in-process compression properties (e.g. tablet weight, dimensions, hardness and friability). The measured data and press settings were recorded in the In-process Run Sheet. If necessary, compression force was adjusted, either higher or lower, to achieve tablets with desired friability and the press was run to complete the tableting operation while sampling and testing of in-process samples at pre-specified intervals.

| TABLETING | |
|---|---|
| Press: Fette 52i Tablet Press | Fill Depth: Variable |
| Label Amount: 30 mg/tablet | Pre Pressure: TBD (target 9.0 mm initially) |
| Target Tablet Weight: 550 mg | |
| Tooling: 12 mm, flat faced, round tooling | Target Main Compression Force: 14 kN |
| Feeder Paddle Speed: 15 rpm | Target Tablet Crushing Strength: 45 N (TBD mm) |
| Turret Speed: 18 rpm | Target Tablet Thickness: Variable |

TABLE 2

Compositions of Amphetamine sulfate IR ODT (Beads) Blends

| Ingredients (mg/tablet) | Amphetamine Sulfate IR ODT (Beads) Blend | | | | |
|---|---|---|---|---|---|
| | ODT A | ODT B | ODT C | ODT D | ODT E |
| Taste-masked Amphetamine IR Beads* | 127.6 | 178.8 | 133.1 | 140.8 | 140.8 |
| Mannitol Granulation | 314.6 | 303.6 | 309.0 | 301.4 | 301.4 |
| Prosolv SMCC 90, Silicified Microcrystalline Cellulose NF | 55.0 | 60.0 | 55.0 | 55.0 | 55.0 |
| Crospovidone NF Type B (Polyplasdone XL-10) | 27.5 | 30.0 | 27.5 | 27.5 | 27.5 |
| Citric Acid | 7.2 | 7.8 | 7.2 | 7.2 | 7.2 |
| Malic Acid | 3.9 | 4.2 | 3.9 | 3.9 | 3.9 |
| Sucralose NF | 3.3 | 3.6 | 3.3 | 3.3 | 3.3 |
| Sodium Stearyl Fumarate NF | 11.0 | 12.0 | 11.0 | 11.0 | 11.0 |
| Total | 550.0 | 600.0 | 550.0 | 550.0 | 550.0 |

*The drug load of the taste-masked IR beads was 23.5% (Formula A), 16.8% (Formula B), 22.5%, 21.3% and 21.3%.

Taste-masking by Solvent Coacervation

Microencapsulation by a solvent coacervation method was utilized to generate Microcap® (amphetamine sulfate and mannitol containing agglomerates with an ethylcellulose coating) to aid in taste-masking of the drug. Mannitol USP was included also as a diluent within the formulation and was chosen because of its particle size, shape and expected compatibility with the drug substance. Ethylcellulose (Standard 100 cps Premium) was utilized as the taste-masking polymer (first membrane) based on suitability with the coacervation process.

The grounded 5-gallon encapsulation tank containing 7500 g of cyclohexane was charged with the ingredients of Formula A in Table 3 [e.g. ethylcellulose (144.0 g), amphetamine sulfate (204.0 g), Mannitol 25 (852.0 g) and polyethylene (127.5 g)]. The agitation in the encapsulation tank was adjusted to 200 rpm. The temperature ramp-up to 80° C. to dissolve ethylcellulose and temperature ramp-down to 30° C. to induce phase separation of ethylcellulose to form a first taste-masking membrane around mannitol amphetamine drug particles were performed per the computer-controlled Heating/Cooling Recipe. The Microcaps® were filtered and rinsed with fresh cyclohexane. The filter cake was evenly spread on stainless steel trays lined with craft paper and dried for approximately 16 hours in a grounded drying rack in drying hood. The dried Microcaps® were passed through a 20 mesh sieve into a labeled container. Following the similar procedure, Microcaps® of Formula B and duplicate batches of Formula C (see Table 3 for compositions) were prepared.

Amphetamine Sulfate Microcaps® formulations were evaluated for particle size, dissolution, assay uniformity and residual solvents. In addition, the degree of taste-masking achieved by each formulation was gauged analytically via a small volume dissolution test. Formulations A and B were suggested to be more taste-masked than Formulation C, however Formulations A and B had significantly larger mean particle size which had the potential to produce a gritty mouth-feel if incorporated into an ODT matrix. Because of this Formulation C was identified to carry forward into further development to improve the effectiveness of taste-masking of the formulation and a duplicate trial was performed.

TABLE 3

Solvent Coacervation Batch Ingredients

| Ingredient (g/batch) | Formula A* | Formula B* | Formula C* |
|---|---|---|---|
| 1 Amphetamine Sulfate | 204.0 | 204.0 | 276.0 |
| 2 Mannitol 25 | 852.0 | 816.0 | 804.0 |
| 3 Ethylcellulose (100 cps) | 144.0 | 180.0 | 120.0 |
| 4 **Cyclohexane (2.54 Gallon) | 7,500 | 7,500 | 7,500 |
| 5 **Polyethylene C10 | 127.5 | 127.5 | 127.5 |
| Batch Size (g): | 1200.0 | 1200.0 | 1200.0 |

*Drug load in Microcaps is 17%, 17% and 23% by weight, respectively in Formula A, B and C while the Ethylcellulose coating is 15%, 12% and 10%, respectively in Formula A, B and C.
**Removed during drying.

Taste-masking of Coacervated Microparticles

EUDRAGIT EPO (112 g) was slowly combined with the Acetone USP (2268 g) in a stainless steel container and mixed using a low shear agitator until a clear solution was obtained. The ethylcellulose (112.0 g) was slowly added and mixing was continued until a clear solution was obtained. The purified water USP (252 g) was added to the solution and followed by adding the dibutyl sebecate NF (28 g) and continuing the mixing for 15 minutes. The magnesium stearate NF (28 g) was added to homogeneously disperse in the solution mixing continued throughout spray.

The coacervated microcapsules (840 g) were loaded into the Glatt GPCG-3 coater (bottom spray (7" in diameter) Wurster insert; 18 mm partition height; 14 mm tubing; 100 mesh screen; Distribution plate: C; Atomization air pressure: 1.5 bar, and nozzle tip size: 1 mm; see preheating parameters—Inlet air temp: 35° C.; Air flow: 16 cfm; Dew point: 2° C.) and coated by spraying the IR coating solution under the following process parameters (Inlet air temp: 35-40° C.; Air flow: 16 cfm; Spray rate: 6-12 ml/mL; Target bed temp: 29-31° C.). and inlet airflow was adjusted to achieve adequate fluidization. The coating solution prepared above was sprayed on to the Amphetamine sulfate Microcaps® while adjusting inlet temperature and airflow parameters to achieve target bed temperature. After 10-20 min, the spray rate was increased while adjusting flow parameters to maintain the target bed temperature. After the entire coating solution was sprayed, the coated beads were dried for 3 minutes at the same processing parameters, discharged and sieved through 60 and 120 mesh screens to discard overs (>20 mesh) and unders (<120 mesh).

Blending and Tableting of Amphetamine sulfate IR ODTs (Microcaps)

One half of the rapidly dispersing granules (see Table 4 for the weights of individual components of the ODT blends) of was added to a 3 L Bin Blender, followed by the IR Beads, Silicified PROSOLV SMCC 90, Microcrystalline Cellulose, Crospovidone, citric acid and malic acid, sucralose and the remaining rapidly dispersing granules to the bin blender and blended for 20 minutes at 20 rpm. The Sodium Stearyl Fumarate was added and blended an additional 5 minutes at 20 rpm. The blend was transferred from the bin blender into a tared and labeled bag.

The hopper of the Fette tablet press (see the table below for tableting parameters) was charged with the blend of Formula ODT A.1, B.1 or C.1 (see Table 4 for details). The fill depth was adjusted to achieve a tablet weight of 600 mg (or 550 mg for Formula D and E). Both pre-compression and main compression forces were, adjusted to achieve tablets with an average crushing strength of 45 N. Tablets of all the formulations were compressed without incidence of defects such as capping, chipping or lamination and all in-process data were recorded in the in-process data sheets.

Tableting Parameters

| | |
|---|---|
| Press: Fette 52i Tablet Press | Fill Depth: TBD |
| Label Amount: 30 mg/tablet | Pre Pressure: TBD, target 9.0 mm initially |
| Target Tablet Weight: 600 mg (or 550 mg) | Target Main Compression Force: 14 kN |
| Tooling: 12 mm, flat faced, round tooling | Target Tablet Crushing Strength: 45N target (TBD mm) |
| Feeder Paddle Speed: 15 rpm | Target Tablet Thickness: tbd |
| Turret Speed: 18 rpm | |

TABLE 4

Blending and Tableting of Amphetamine sulfate IR ODTs (Microcaps ®)
Amphetamine Sulfate (Microcaps ®) IR ODT Blend
Machine Configuration: 3 L Bin Blender ID: IBC-3402

| Ingredients (mg/tablet) | ODT A.1 | ODT C.1 | ODT C.1 |
|---|---|---|---|
| Amphetamine Sulfate (Microcaps ®) | 176.5 | 175.4 | 175.4 |
| Rapidly Dispersing Granules | 306.0 | 307.2 | 307.2 |
| Prosolv SMCC 90, Silicified Micrcrystalline Cellulose NF | 60.0 | 60.0 | 60.0 |
| Crospovidone NF (Polyplasdone XL-10) Type B | 30.0 | 30.0 | 30.0 |
| Citric Acid USP | 7.8 | 7.8 | 7.8 |
| Malic Acid USP | 4.2 | 4.2 | 4.2 |
| Sucralose NF | 3.6 | 3.6 | 3.6 |
| Sodium Stearyl Fumarate NF | 12.0 | 12.0 | 12.0 |
| Total | 600.0 | 600.0 | 600.0 |

Figure 3:
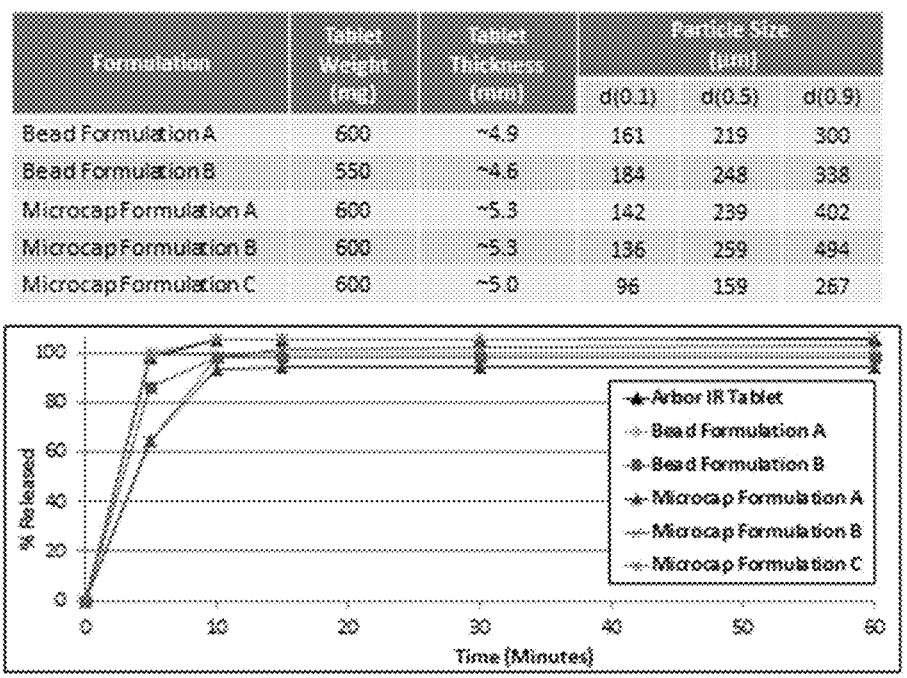
FIG. 3 shows the tablet weight and thickness of ODTs and particle size distribution data for taste-masked amphetamine sulfate of Bead Formula A & B, Microcaps Formula A, B & C (top) and in vitro amphetamine dissolution profiles from (1) EVEKEO® (Arbor Pharmaceuticals' racemic amphetamine sulfate IR tablets) and IR ODTs containing taste-masked amphetamine sulfate of Bead Formula A & B and Microcaps Formula A, B, & C (bottom).

FIG. 3 shows the tablet weight and thickness of ODTs and particle size distribution data for the previously identified taste-masked amphetamine sulfate microparticles of Bead Formula A & B, or Microcaps® Formula A, B & C (top) and in vitro amphetamine dissolution profiles from (1) EVEKEO® (racemic amphetamine sulfate IR tablets) and IR ODTs containing taste-masked amphetamine sulfate microparticles of Bead Formula A & B and Microcaps® Formula A, B, & C (bottom).

Amphetamine sulfate is freely soluble and all the ODT batches were observed to release amphetamine within 15 minutes. Hence, the dissolution was not considered to be a critical factor in the selection the formulation for commercialization. The selection should be based on meeting the specifications for organoleptic properties including drug taste, non-gritty mouthfeel and robustness of the manufacturing process. Table 5 presents the particle size data in terms of d(0.1), d(0.5) and d(0.9) for taste-masked IR beads (Formula A and B) and Microcaps® (Formula A, B and C) and Sip test data for taste-masked beads (Formula A and B), Microcaps® (Formula A, B and C) and the corresponding ODT batches containing these taste-masked microparticles. The Sip test values for Formula ODT C (Microcaps®) were slightly higher than that for Formula ODT A (Beads). A higher Sip test value suggested a higher probability of experiencing the drug taste on exposure to saliva in the buccal cavity. However, the Sip test was not yet validated. Hence, based on the particle size data of the taste-masked microparticles (Beads and Microcaps®), the corresponding ODTs Formula ODT A (Beads) and ODT C (Microcaps®) were judged to be suitable for advancing into further development.

TABLE 5

Particle size data for taste-masked IR beads and Microcaps ® and Sip test data for taste-masked beads, Microcaps ® and ODTs containing these taste-masked microparticles

| Taste-masked Particles | Particle Sizing (µm) | | | Sip Test (Ranking) | |
|---|---|---|---|---|---|
| | D(0.1) | D(0.5) | D(0.9) | Microcaps | ODT |
| Beads Formula A | 161 | 219 | 300 | 0.3% | 1.4% |
| Beads (CTM) | 180 | 246 | 336 | NT | NT |
| Beads Formula B | 184 | 248 | 338 | 0.04-0.12% | 1.8% |
| Microcaps ® A | 142 | 239 | 402 | NT | 2.5% |
| Microcaps ® B | 136 | 259 | 494 | 6.2-6.4% | 3.1% |
| Microcaps ® C | 96 | 159 | 267 | 8.0-9.2% | 3.4% |
| Duplicate Microcaps ® C | 149 | 236 | 376 | NT | NT |
| Microcaps ® (CTM) | 128 | 191 | 287 | NT | NT |

*d(0.1), d(0.5) and d(0.9) denote the mean particle size, respectively, of the 10%, 50% and 90% of the particles;
NT—not determined.

Example 2

30 mg Amphetamine sulfate IR ODTs based on taste-masked IR beads and IR Microcaps® were manufactured utilizing the fluid-bed coater, Glatt GPCG 5 for the preparation of IR beads or 5 Gallon Coacervation System for microencapsulation of amphetamine sulfate-mannitol agglomerates, and Glatt GPCG 3, 7 L Bin blender, and Fette tablet press, respectively, for taste-masking coating, blending and tableting (see Table 6 for compositions for each of the steps). Both the ODT batches were compressed using the Fette tablet press. The hopper was charged with the blend. Adjusted fill depth to achieve target tablet weight of 550 mg (for ODTs containing Beads or 600 mg for ODTs containing Microcaps®). Both pre-compression and main compression forces were adjusted to achieve tablets with an average crushing strength of 45 N. Once achieved, the tablet press was operated in 'auto' mode and NLT 45 tablets were collected for testing for in-process compression properties (e.g. tablet weight, dimensions, hardness and friability). The measured data and press settings were recorded in the In-process Run Sheet. The tablets were release tasted using qualified analytical methods. The clinical trial material [e.g. HDPE bottles containing 30 mg Amphetamine Sulfate IR ODTs (Beads) vs. 30 mg Amphetamine Sulfate IR ODTs (Microcaps)] was shipped to Senopsys LLC to support the planned organoleptic taste testing.

TABLETING

| | |
|---|---|
| Press: Fette 52i Tablet Press | Fill Depth: TBD |
| Label Amount: 30 mg/tablet | Pre Pressure: TBD, target 9.0 mm initially |
| Target Tablet Weight: 550 mg or 600 mg | Target Main Compression Force: 14 kN |
| Tooling: 12 mm, flat faced, round tooling | Target Tablet Crushing Strength: 45N |

-continued

TABLETING

| | |
|---|---|
| Feeder Paddle Speed: 15 rpm | initial target (TBD mm) |
| Turret Speed: 18 rpm | Target Tablet Thickness: tbd |

TABLE 6A

Manufacture of Amphetamine sulfate IR Beads or Microcaps ® ODTs

| Ingredient | % Batch Taste-masking of IR Beads | Quantity/Batch Taste-masking of IR Beads | % Batch Taste-masking of Microcaps ® | Quantity/Batch Taste-masking of Microcaps ® |
|---|---|---|---|---|
| IR Beads/Microcaps | 75 | 0.840 | 75 | 0.840 |
| EUDRAGIT EPO | 10 | 0.112 | 10 | 0.112 |
| Ethylcellulose 10 cps | 10 | 0.112 | 10 | 0.112 |
| Magnesium stearate | 2.5 | 0.028 | 2.5 | 0.028 |
| Dibutyl sebacate | 2.5 | 0.028 | 2.5 | 0.028 |
| Acetone | | 2.268* | | 2.268* |
| Purified Water | | 0.252* | | 0.252* |
| Total | 100.00 | 1.120 | 100.00 | 1.120 |

*Removed during drying

TABLE 6B

Manufacture of Taste-masked Amphetamine sulfate IR Beads or Microcaps ®

| Ingredient | % Batch Taste-masking of IR Beads | Quantity/Batch Taste-masking of IR Beads | % Batch Taste-masking of Microcaps ® | Quantity/Batch Taste-masking of Microcaps ® |
|---|---|---|---|---|
| IR Beads/Microcaps | 75 | 0.840 | 75 | 0.840 |
| EUDRAGIT EPO | 10 | 0.112 | 10 | 0.112 |
| Ethylcellulose 10 cps | 10 | 0.112 | 10 | 0.112 |
| Magnesium stearate | 2.5 | 0.028 | 2.5 | 0.028 |
| Dibutyl sebacate | 2.5 | 0.028 | 2.5 | 0.028 |
| Acetone | | 2.268* | | 2.268* |
| Purified Water | | 0.252* | | 0.252* |
| Total | 100.00 | 1.120 | 100.00 | 1.120 |

*Removed during drying

TABLE 6C

Manufacture of Amphetamine sulfate IR ODTs (Beads) or ODTs (Microcaps ®)

| Ingredient | mg/Batch 30 mg IR ODTs (Beads) | Quantity/Batch 30 mg IR ODTs (Beads) | Mg/Batch 30 mg IR ODTs (Microcaps) | Quantity/Batch 30 mg IR ODTs (Microcaps) |
|---|---|---|---|---|
| Taste-masked Beads/Microcaps | 133.32 | 0.4363 | 173.94 | 0.5798 |
| Mannitol Granulation | 308.88 | 1.0109 | 308.46 | 1.0282 |
| PROSOLV SMCC 90 | 55.00 | 0.1800 | 60.00 | 0.2000 |
| Crospovidone | 27.5 | 0.0900 | 30.00 | 0.1000 |
| Citric Acid Anhydrous | 7.15 | 0.0234 | 7.80 | 0.0260 |
| Malic Acid | 3.85 | 0.0126 | 4.20 | 0.0140 |
| Sucralose | 3.30 | 0.0108 | 3.60 | 0.252* |
| Sodium Stearyl Fumarate | 11.0 | 0.0360 | 12.00 | 0.400 |
| Total | 550.00 | 1.800 | 600.00 | 2.000 |

An open-label comparative sensory organoleptic taste assessment of 30 mg Amphetamine Sulfate IR ODT (Beads) vs. 30 mg Amphetamine Sulfate IR ODT (Microcaps) was performed by five healthy qualified Panelists under pre-approved clinical protocol (New England Independent Review Board) and established "Flavor Profile Method" (Keane, P. The Flavor Profile Method. In C. Hootman (Ed.), Manual on Descriptive Analysis Testing for Sensory Evaluation ASTM Manual Series: MNL 13. Baltimore, Md. (1992)) (FIG. 10).

The samples were evaluated as follows:

1. One 30 mg amphetamine sulfate ODT to be evaluated was placed in each panelist's hand.
2. Starting at the same time, panelists placed the tablet on the tongue and a timer was started. The tablet was gently rolled against the roof of the mouth with the tongue without biting, continuing until the last granule was melted to the point of swallowing. The material left in the mouth was then expectorated and the disintegration time was recorded.
3. The panelists then independently evaluated and recorded the initial taste and aftertaste characteristics at periodic intervals up to 30 minutes as flavor persisted.
4. The panelists recited their individual results and a preliminary Flavor Profile was generated for the sample.
5. On a separate day, Steps 1 through 4 were repeated for a second sample using the preliminary Flavor Profile from Step 4 as a guide, with the panelists making any necessary modifications.
6. The panelists recited their individual results and a final Flavor Profile was developed for the sample.

The samples were evaluated in the following order:

| Sample Order | Rep | Description |
| --- | --- | --- |
| 1 | 1 | Amphetamine Sulfate 30 mg ODT (Bead) |
| 2 | 2 | Amphetamine Sulfate 30 mg ODT (Bead) |
| 3 | 1 | Amphetamine Sulfate 30 mg ODT (Microcap) |
| 4 | 2 | Amphetamine Sulfate 30 mg ODT (Microcap) |

Samples labeled "Bead" are taste-masked by fluid-bed coating the IR beads, whereas samples labeled "Microcap®" are taste-masked by fluid-bed coating the coacervated Microcap® as described above.

The following Tables show the comparative flavor/aftertaste (bitterness) Profile results.

TABLE 7

Flavor Profile Amphetamine sulfate IR ODTs (Beads)

Flavor Profile Amphetamine ODT (30 mg/Tablet)-Lot #PF56810001 Bead

|  | Initial | 1 Min | 3 Min | 5 Min | 10 Min | 15 Min | 20 Min | 25 Min | 30 Min |
| --- | --- | --- | --- | --- | --- | --- | --- | --- | --- |
| Sweet (5) | 1½ | 1 | ½ | 0-½ | — | — | — | — | — |
| Sour (5) | 2 | 1½ | ½ | ½ | — | — | — | — | — |
| Cardboard Aromatic (4) | ½ | — | — | — | — | — | — | — | — |
| Burnt Poly Aromatic (4) | 1 | ½ | — | — | — | — | — | — | — |
| Chalky Mouthfeel (3) | 1-1½ | 1 | — | — | — | — | — | — | — |
| Bitter (4) | 1½ | 1½-2 | 1 | 1 | ½ | ½ | — | — | — |
| Tongue Sting Mouthfeel (3) | — | 1 | ½ | ½ | 0-½ | — | — | — | — |
| Drying Mouthfeel (3) | — | 1 | 1½ | 1-1½ | 1 | 1 | ½ | — | — |
| Gritty Texture (5) | 1 | — | — | — | — | — | — | — | — |

| Flavor Leadership Interpretation | | | | |
| --- | --- | --- | --- | --- |
| 1-Aromatic Identity | 2-Amplitude | 3-Mouthfeel | 4-Off-Notes | 5-Aftertaste |
| Not applicable for unflavored products | Not applicable for unflavored products | Slight-to-moderate intensity chalky, slight intensity drying and tongue sting mouthfeels. | Slight-to-moderate intensity bitterness and slight intensity burnt poly and cardboard aromatic off-notes. | Lingering bitter, sweet and sour basic tastes and mouthfeels |

TABLE 8

Flavor Profile Amphetamine sulfate IR ODTs (Microcaps ®)

Flavor Profile Amphetamine ODT (30 mg/Tablet)-Lot #PF57010001 Microcap

|  | Initial | 1 Min | 3 Min | 5 Min | 10 Min | 15 Min | 20 Min | 25 Min | 30 Min |
| --- | --- | --- | --- | --- | --- | --- | --- | --- | --- |
| Sweet (5) | 1½ | 1 | ½-1 | 0-½ | — | — | — | — | — |
| Sour (5) | 2 | 1-1½ | ½ | 0-½ | — | — | — | — | — |
| Cardboard Aromatic (4) | ½-1 | — | — | — | — | — | — | — | — |
| Chalky Mouthfeel (3) | 1½ | ½ | ½ | — | — | — | — | — | — |
| Bitter (4) | 1-1½ | 1 | ½ | ½ | — | — | — | — | — |

TABLE 8-continued

Flavor Profile Amphetamine sulfate IR ODTs (Microcaps ®)

| | | | | | | | | | |
|---|---|---|---|---|---|---|---|---|---|
| Drying Mouthfeel (3) | — | 1 | 1½ | 1-1½ | 1 | ½-1 | — | — | — |
| Gritty Texture (5) | ½ | — | — | — | — | — | — | — | — |

Flavor Leadership Interpretation

| 1-Aromatic Identity | 2-Amplitude | 3-Mouthfeel | 4-Off-Notes | 5-Aftertaste |
|---|---|---|---|---|
| Not applicable for unflavored products | Not applicable for unflavored products | Slight-to-moderate intensity chalky bitterness and slight drying mouthfeel | Slight-to-moderate intensity bitterness and very slight intensity cardboard aromatic off-notes. | Lingering bitter, sweet and sour basic tastes and mouthfeels |

Figure 4:
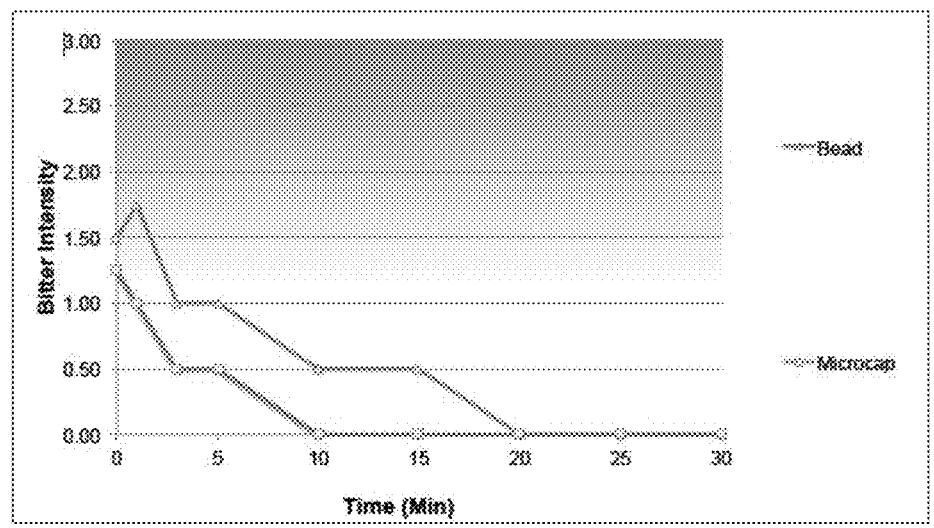
FIG. 4 shows that the Amphetamine sulfate IR ODTs (Microcaps®) had a lower overall bitterness profile than the Amphetamine sulfate IR ODTs (Beads), which dropped below a patient perceptible intensity (<1) at 1 minute in the aftertaste vs. 5 minutes for the ODTs (Beads).

FIG. 4 shows the comparative flavor/aftertaste (bitterness) Profile results. The conclusion from the study was that the orally disintegrating pharmaceutical composition (taste-masked Microcaps®) of the invention has an average patient perceptible intensity of bitterness of less than 1 minute when the orally disintegrating composition (taste-masked IR beads) having a dose equivalent to 30 mg of racemic amphetamine sulfate is evaluated by the sensory panel using the flavor profile method. In fact, it was shown that the 30 mg Amphetamine Sulfate IR ODTs (Microcaps®) had a lower overall bitterness profile than the corresponding 30 mg ODTs (Beads), which dropped below a patient perceptible intensity (<1) at 1 minute in the aftertaste vs. 5 minutes for the ODT (Beads). Although both 30 mg Amphetamine Sulfate IR ODTs were unflavored, the ODTs (Microcaps) were slightly higher in flavor quality than the ODTs (Beads), due to lower bitterness (primary), aromatic off-note (secondary) and mouthfeel (tertiary) profiles. Tables 7-8 and FIG. 4 show that the Amphetamine sulfate IR ODTs (Microcaps) had a lower overall bitterness profile than the Amphetamine sulfate IR ODTs (Beads), which dropped below a patient perceptible intensity (<1) at 1 minute in the aftertaste vs. 5 minutes for the ODTs (Beads). Based on the organoleptic taste testing, particle size and dissolution properties, the Formula ODT C.1 was selected for advancing into testing of robustness of the manufacturing process.

Example 3

Figure 2:
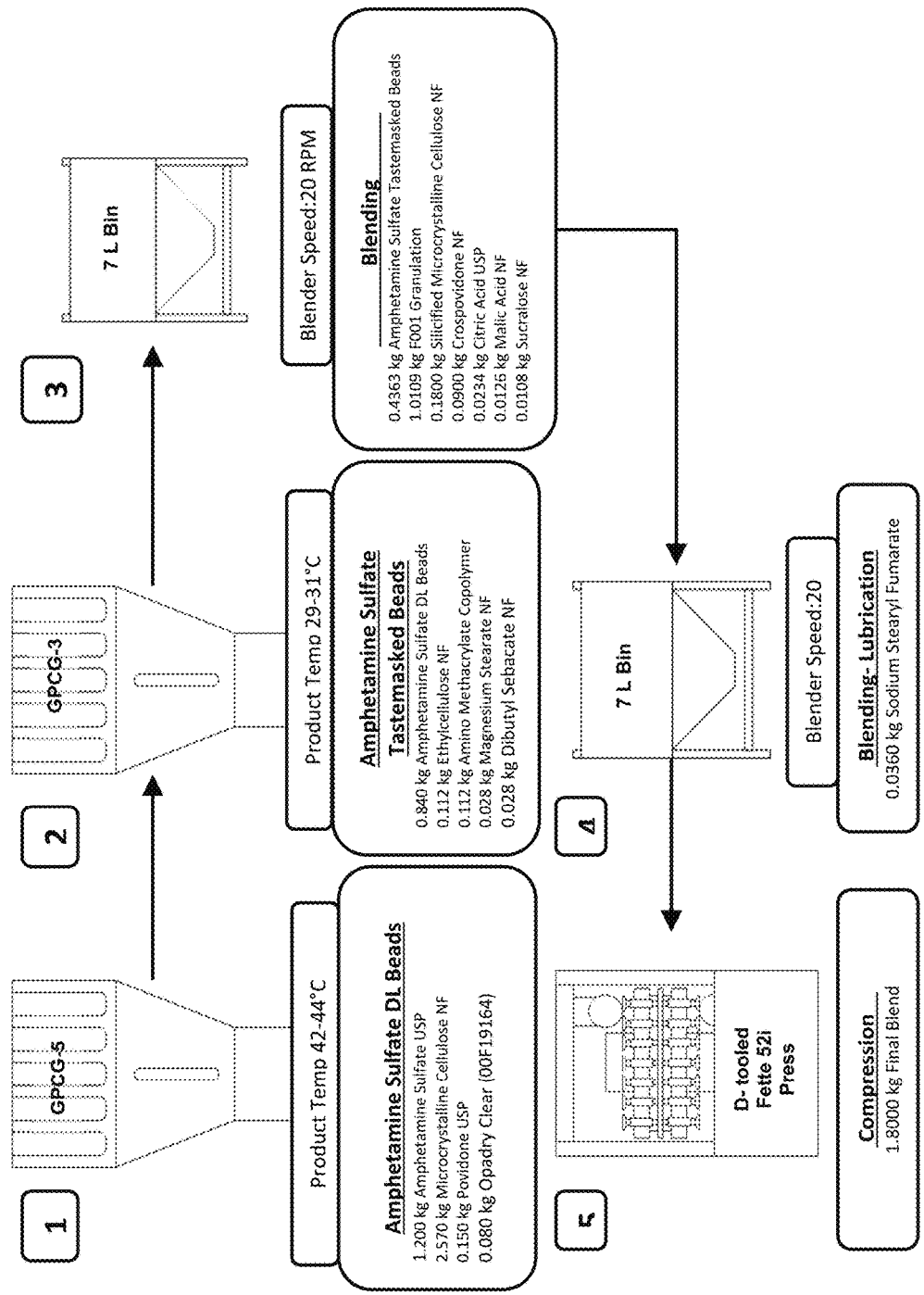
FIG. 2 shows the process equipment train used for the manufacture of immediate release orally disintegrating tablets (IR ODTs) containing well taste-masked racemic amphetamine sulfate microparticles IR Beads (top) and Microcaps® (bottom).

Manufacture of Amphetamine sulfate IR ODTs at $\frac{1}{10}^{th}$ Commercial Scale Manufacture of the Amphetamine Sulfate IR ODT followed the manufacturing process train outlined in FIG. 2, excepting that the internal lubrication step (Step 4) was omitted and the die and punch surfaces were sprayed on with the magnesium stearate at a spray rate of 3.0 g/min prior to each compression in Step 5.

Manufacture of Taste-masked Amphetamine Sulfate Microcaps®

The 200 gallon Solvent System (Batch size: 48 kg) containing cyclohexane (125 gallons) was charged with mannitol (MANNITOL 25; 32.2 kg), racemic Amphetamine sulfate (11.04 kg), Ethylcellulose NF (Standard 100 Premium; 4.80 kg) and polyethylene (EPOLENE C10; 6.0 kg) while agitating at 75 rpm. The contents of the coacervation tank were subjected to the computer-controlled Heating/Cooling Recipe program to complete the microencapsulation process and the resultant Amphetamine Sulfate Microcaps® were then filtered through a rotary vacuum filter and rinsed with fresh cyclohexane to remove residual polyethylene. The Microcaps filtrate was then dried in a fluid bed dryer via an automated, pre-programmed drying process. Once dried, the Amphetamine Sulfate Microcaps® were passed through a 20 mesh screen using a vibrating siever into properly labeled fiber drums, double lined with low density polyethylene bags.

For Microcaps Fluid-bed Coating (Batch size: 56.0 kg), Eudragit EPO (5.6 kg) was added to Acetone (113.4 kg) and mixed using an agitator at approximately 300 rpm±25 rpm in a grounded stainless steel tank for NLT 10 minutes to dissolve completely. Ethylcellulose 10 cps (5.6 kg) was slowly added to the tank and continued to mix for NLT 10 minutes to dissolve completely. Purified Water USP (12.6 kg) was slowly added to the tank. Dibutyl Sebacate (1.4 kg) was slowly added to the tank and continued to mix for NLT 30 minutes and Magnesium Stearate (1.4 kg) was slowly added to the tank and mixed at approximately (750±25) rpm and continued to mix with moderate agitation throughout spray. When the taste-masked coating solution was complete, approximately 0.5 kg of Acetone was sprayed to rinse the spraying lines, and the taste-masked beads were dried for 3 minutes at the same processing parameters and discharged via 20 MG mesh (oversize) and 120 MG mesh (undersize) screens of the sifter into 41 gallon drums, double lined with 4 mil polyethylene bags, under the discharge port.

Taste-masking by Coating in Glatt GPCG 120

| | |
|---|---|
| Product bowl with 18" Wurster bottom spray | Nozzle Tip Port Size: 1.5 mm |
| Air distribution plate: Inner: G; Outer: C | Product Support Screen: 200 mesh |
| Process Air Volume: 600 cfm (472-800 cfm) | Process Air Temperature: 45° C. (30-60° C.) |
| Peristaltic Pump Tubing Size/Spray Nozzle | Tubing Size: Masterflex 24, Pharm Med. |
| Spray Rate: 550 g/min (ramp up 100-650 g/min) | Product Temperature: 29-31° C. (25-40° C.) |

Manufacture of Amphetamine IR ODT Blend

The Amphetamine Sulfate Immediate Release (IR) blend (see Table 9 for composition) was prepared by vacuum charging approximately half of the mannitol granulation into a bin blender equipped with a 300 L bin followed by the Amphetamine Sulfate Taste-masked Microcaps, crospovidone NF, silicified microcrystalline cellulose NF, sucralose NF, malic acid NF and citric acid anhydrous USP. The silicified microcrystalline cellulose NF, sucralose NF, malic acid NF and citric acid anhydrous USP were delumped through a conical mill fitted with a round 0.094" screen operating at approximately 60 Hz prior to being added to the bin. The remaining half of the mannitol granulation was then added to the bin. The material was blended for approximately 21 minutes at 10 rpm to achieve a homogeneous blend. Once blended, the blend was discharged into fiber drums, double lined with LDPE bags.

TABLE 9

Composition of Taste-masked Amphetamine Sulfate IR ODT Blend

| Ingredients/Intermediates of IR ODTs (Microcaps) | Tablet (%) | Quantity (kg) |
|---|---|---|
| Amphetamine Sulfate Taste-masked Microcaps ® | 29.0 | 36.0 |
| Rapidly Dispersing Microgranules (Mannitol Granulation)* | 53.4 | 66.2 |
| Prosolv SMCC 90, Silicified Microcrystalline Cellulose NF | 10.0 | 12.4 |
| Crospovidone NF (Polyplasdone XL-10) Type B | 5.0 | 6.20 |
| Citric Acid, Anhydrous USP Fine Granular | 1.3 | 1.61 |
| Malic Acid NF | 0.7 | 0.87 |
| Sucralose NF | 0.6 | 0.74 |
| Total | 100.0 | 124.0 |

*Mannitol granulation is an excipient pre-mix containing mannitol USP and crospovidone NF at a ratio of 95/5 and is manufactured using a validated high-shear granulation process.

The Amphetamine Sulfate IR ODT, 30 mg were compressed using a rotary tablet press equipped with a force feeder and 12.00 mm, round, flat faced, radius edge tooling with embossed upper and lower punches. The press was equipped with an external lubrication system which sprayed an external processing aid, magnesium stearate NF, at a rate of approximately 3.0 g/min onto the upper and lower punch tips as well as the die wall to maintain adequate lubrication throughout the process. The blend was vacuum transferred from bulk drums into the hopper of the press. Tablets are compressed to a target tablet weight of 600 mg (range 570-630 mg) according to the compression parameters listed in Table 10 to produce tablets within the designated ranges for weight, hardness and friability. During compression, tablet samples were collected at approximately 18,700 tablet intervals as Composite Sample and tested for appearance, average weight/10 tablets, individual tablet weight, thickness, hardness and friability to ensure that the tablets met the established in-process control acceptance criteria. As the tablets were discharged from the press, the tablets were passed through a tablet de-duster to remove any excess magnesium stearate NF and then through a metal detector into properly labeled drums double lined with low density polyethylene bags.

TABLE 10

Compression Parameters/Tablet Attributes for Amphetamine Sulfate IR ODT, 30 mg

| Parameter/Attribute | Target | Range |
|---|---|---|
| Main Compression Force (kN) | 9.5* | N/A |
| Fill Depth (mm)*** | 9.10* | N/A |
| Force Feeder (%) | 70 | N/A |
| Turret Speed (rpm) | 25* | NMT 30 RPM |
| External Lubrication (g/min) | 3.0* | N/A |
| Average Weight/10 Tablets (g) | 6.00 | 5.70-6.30 |
| Individual Tablet Weight (mg) | 600 | 570-630 |
| Hardness (N) | 55 | 32-80 |
| Thickness (mm) | 5.20 | FIO** |
| Friability (% loss) | NMT 0.4 | NMT 1.0 |

To Demonstrate Robustness of the Manufacturing Process Train

Based on a risk assessment of the process, development at the 200 gallon scale investigated the influence of tank agitation and polyethylene level on quality attributes of the intermediate. Tank agitation was varied from 65 to 85 rpm and polyethylene level was varied from 1.5% to 1.75% w/w. Of the six batches manufactured, all batches exhibited acceptable assays of above 97%, with residual cyclohexane and polyethylene values well below the acceptance criteria (Residual Cyclohexane range: <LOQ-67 ppm; Residual polyethylene range: 0.4-1.25%). In addition, a linear relationship was observed between the particle size distribution of the microcaps and process parameters of percent polyethylene and tank agitation. At the process parameter ranges investigated, particle sizes of the resultant microcaps produced at the 200 gallon scale fell within the ranges of the particle size distributions observed during development at the 5 gallon scale. These analytical results suggest that manufacturing over the range of polyethylene level and tank agitation investigated would produce acceptable Amphetamine Sulfate Microcaps® capable of meeting the acceptance criteria for the intermediate quality attributes. Based on this information, a target tank agitation of 75 rpm and a target polyethylene level of 1.6% w/w, both at approximate center points over the ranges investigated, were deemed optimal for the process.

The risk assessment of the entire process train for the production of the Amphetamine Sulfate IR ODTs suggested a low risk associated with the fluid-bed coating. To further demonstrate the robustness of the process train, the process was challenged for 5 min by having the Inlet Air temperature (target: 54° C.) at 40° C. or 70° C.; Process Air Volume (target: 500 cfm) at 400 or 650 cfm; dew point (target: 8° C.) at 4° C. or 15° C.; and Atomization Air Pressure (target: 2.1 bar) at 1.9 bar or 2.3 bar. All six development batches manufactured at the 56.0 kg scale in the Glatt met the acceptance criteria for the quality attributes (e.g. assay, residual acetone, and particle size) including those batches that underwent the processing parameter challenge.

All individual drum uniformity values for four Amphetamine Sulfate Tastemasked Microcaps® sampled Top, Middle and Bottom, were well within 90-110% of the theoretical assay with both batches exhibiting % RSD of less than 0.5%.

The Amphetamine Sulfate IR Blend was scaled from a 7 L Bin to a 300 L bin (124.0 kg Batch Size). For the commercial 300 L scale at the 124.0 kg batch size, blend time experiments were studied. Two blends were evaluated. Samples were pulled for the first blend at three different time intervals and the bin was sampled using a dose uniformity thief at 10 separate locations in the bin. For all locations evaluated, both individual and average assays were within 90.0-110.0% of theoretical (4.5%-5.5%) with a % RSD of NMT 3.2% being observed with the minimum % RSD being achieved at the target blend time of 21 min for both blends evaluated. Based on this information, a blend time of 21 min at 10 rpm was considered optimal for the process.

The tablet press was equipped with a force-feeder and 12 mm round, flat-face radius edge tooling with embossed upper and lower punches. Process development for the 30 mg strength utilized a $2^3$ factor design with three center points as part of a Design of Experiments (DOE) screening study. Process variables investigated were Turret Speed (Range: 20-30 rpm), Main Compression Force (Range: 7-12 kN) and Force Feeder Speed (Range: 70-90%). The DOE design was executed in the order provided in the design matrix. For each of the 11 sub batches, the press was set to the variable targets and the main compression force allowed to equilibrate prior to samples being taken. Tablets were tested for quality attributes of friability USP<1216> hardness, thickness, appearance, assay and disintegration time USP<701>. Data from the DOE sub batches manufactured showed a very robust process. Batches were successfully completed without issue and yielded tablets capable of achieving the desired quality attributes across the process ranges investigated. Despite the wide range in tablet hardness, friability of the amphetamine sulfate tablets were able to meet the specification of NMT 1.0% for friability and disintegration of the ODT's were observed to be NMT 20 seconds for all sub-batches and would meet the specification of NMT 30 seconds. Dissolution results for the sub-batches confirmed that the product rapidly released as designed for an immediate release dosage form.

Example 4

Manufacture of Amphetamine IR ODT Bioequivalence & Registration Stability Batches Manufacture of the Amphetamine Sulfate IR ODT followed the process train outlined in Example 3 above.

Manufacture of Taste-masked Amphetamine Sulfate Microcaps®

The 200 gallon Solvent System (see Table for composition; Batch size: 48 kg) containing cyclohexane (125 gallons) was charged with mannitol (32.2 kg), racemic Amphetamine sulfate (11.04 kg), Ethylcellulose 100 cps (4.80 kg) and polyethylene (6.0 kg) while agitating at 75 rpm. The contents of the coacervation tank were subjected to the computer-controlled Heating/Cooling Recipe program and the resultant Amphetamine Sulfate Microcaps® were then filtered through a rotary vacuum filter, rinsed with fresh cyclohexane to remove residual polyethylene, and dried in a fluid bed dryer via an automated, pre-programmed drying process. Once dried, the Amphetamine Sulfate Microcaps® were passed through a 20 mesh screen using a vibrating siever into properly labeled fiber drums, double lined with low density polyethylene bags.

For Microcaps® Fluid-bed Coating, EUDRAGIT EPO (5.6 kg) was added to Acetone (113.4 kg) and mixed using an agitator at approximately 300 rpm±25 rpm in a grounded stainless steel tank for NLT 10 minutes to dissolve completely. Ethylcellulose 10 cps (5.6 kg) was slowly added to the tank and continued to mix for NLT 10 minutes to dissolve completely. Purified Water USP (12.6 kg) was slowly added to the tank. Dibutyl Sebacate (1.40 kg) was slowly added to the tank and continued to mix for NLT 30 minutes and Magnesium Stearate (1.4 kg) was slowly added to the tank and mixed at approximately 250 rpm±25 rpm and continued to mix with moderate agitation throughout spray. The Glatt GPCG 120 [Product bowl with 18" Wurster bottom spray, Air distribution plate: Inner: G; Outer: C; Product Support Screen: 200 mesh; Partition Height from Distribution Plate: 45±2 mm; Nozzle Tip Port Size: 1.5 mm; Peristaltic Pump Tubing Size/Spray Nozzle Tubing Size: Masterflex 24, Pharm Med. Process Air Temperature: 450° C. (30-60° C.); Process Air Volume: 600 cfm (472-800 cfm); Spray Rate: 550 g/min (ramp up 100-650 g/min); Product Temperature: 29-31° C. (25-40° C.). When the taste-masked coating solution was complete, approximately 0.5 kg of Acetone was sprayed to rinse the spraying lines, and the taste-masked beads were dried for 3 minutes at the same processing parameters and discharged via 20 MG mesh (oversize) and 120 MG mesh (undersize) screens of the sifter into 41 gallon drums, double lined with 4 mil polyethylene bags, under the discharge port.

Manufacture of Amphetamine IR ODT Blend

A detailed overview of the manufacturing steps for the Amphetamine Sulfate Immediate Release (IR) blend process is provided below, referencing the flowchart illustrated in FIG. 2. The blend (see Table 11 for composition) was prepared by vacuum charging approximately half of the mannitol granulation into a bin blender equipped with a 300 L bin followed by the Amphetamine Sulfate Taste-masked Microcaps®, crospovidone NF, silicified microcrystalline cellulose NF, sucralose NF, malic acid NF and citric acid anhydrous USP. The silicified microcrystalline cellulose NF, sucralose NF, malic acid NF and citric acid anhydrous USP were delumped through a conical mill fitted with a round 0.094" screen operating at approximately 60 Hz prior to being added to the bin. The remaining half of the mannitol granulation was then added to the bin. The material was blended for approximately 21 minutes at 10 rpm to achieve a homogeneous blend. Once blended, the blend was discharged into fiber drums, double lined with LDPE bags.

TABLE 11

Composition of Taste-masked Amphetamine Sulfate IR ODT Blend

| Ingredients/Intermediates of IR ODTs (Microcaps) | Tablet (%) | Quantity (kg) |
|---|---|---|
| Amphetamine Sulfate Taste-masked Microcaps ®* | 29.0 | 36.0 |
| Rapidly Dispersing Microgranules (Mannitol Granulation)* | 53.4 | 66.2 |
| Prosolv SMCC 90, Silicified Microcrystalline Cellulose NF | 10.0 | 12.4 |
| Crospovidone NF (Polyplasdone XL-10) Type B | 5.0 | 6.20 |
| Citric Acid, Anhydrous USP Fine Granular | 1.3 | 1.61 |
| Malic Acid NF | 0.7 | 0.87 |
| Sucralose NF | 0.6 | 0.74 |
| Total | 100.0 | 124.0 |

*Mannitol granulation is an excipient pre-mix containing mannitol USP and crospovidone NF at a ratio of 95/5 and is manufactured using a validated high-shear granulation process.

The Amphetamine Sulfate IR ODTs, 20 mg were compressed using a rotary tablet press equipped with a force feeder and 10.48 mm, round, flat faced, radius edge tooling with embossed upper and lower punches. The press was equipped with an external lubrication system which sprayed an external processing aid, magnesium stearate NF, at a rate of approximately 3.0 g/min onto the upper and lower punch tips as well as the die wall to maintain adequate lubrication throughout the process. The blend was vacuum transferred from bulk drums into the hopper of the press. Tablets were compressed to a target tablet weight of 400 mg (range 380-420 mg) according to the compression parameters listed in Table 12 to produce tablets within the designated ranges for weight, hardness and friability. The registration stability IR ODT batches of 5 mg, 10 mg, 15 mg, 20 mg, 30 mg and 40 mg Amphetamine Sulfate Immediate Release ODTs having dose proportional tablet weights were compressed using the common ODT blend as described above. Each batch was compressed using a pre-programmed recipe that regulated the fill depth as needed to maintain the main compression within a target adjust tolerance. Press automatically rejected any tablets that exceed the high or low rejection force tolerance.

TABLE 12

Compression Parameters and Tablet Attributes for Amphetamine Sulfate IR ODT, 20 mg Parameter/Attribute

|  | Target | Range |
|---|---|---|
| Compression Parameter |  |  |
| Main Compression | 7.0 kN* | N/A |
| Fill Depth (mm) | 7.82* | N/A |
| Force Feeder (%) | 70 | N/A |
| Turret Speed (rpm) | 30* | NMT 40 RPM |
| External Lubrication (g/min) | 3.0* | N/A |
| Tablet Attributes |  |  |
| Average Weight/10 Tablets | 4.0 g | 5.70-6.30 |
| Individual Tablet Weight | 400 mg | 380-420 |
| Hardness (N) | 36 | 21-57 |
| Thickness (mm) | 4.54 | FIO** |
| Friability (% loss) | NMT 0.4 | NMT 1.0 |
| Appearance | No defects | No defects |

Figure 5:
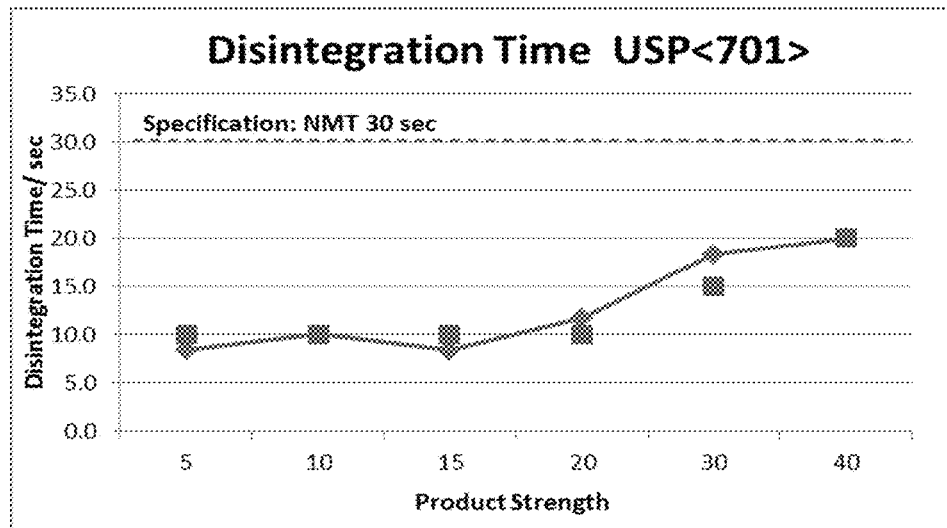
FIG. 5 shows the disintegration time as a function of compression force used to compress tablets of the registration stability batches when tested for disintegration time by United States Pharmacopeia (USP) Method <701>.
Figure 6:
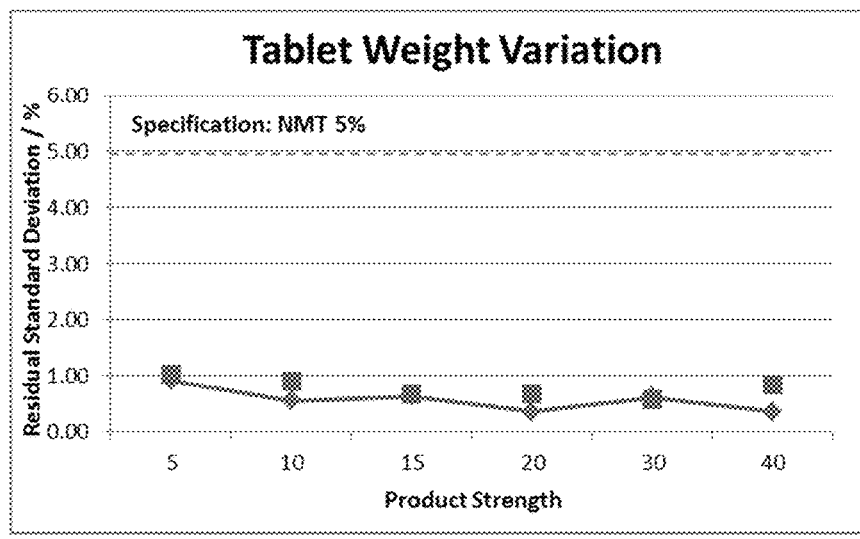
FIG. 6 shows the weight variation as a function of compression force used to compress tablets of the registration stability batches.
Figure 7:
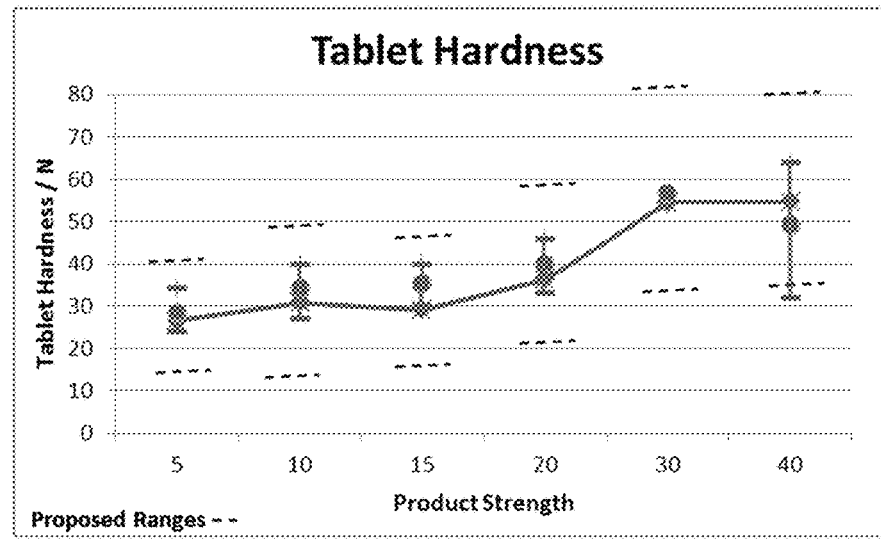
FIG. 7 shows the tablet hardness as a function of compression force used to compress tablets of the registration stability batches.
Figure 8:
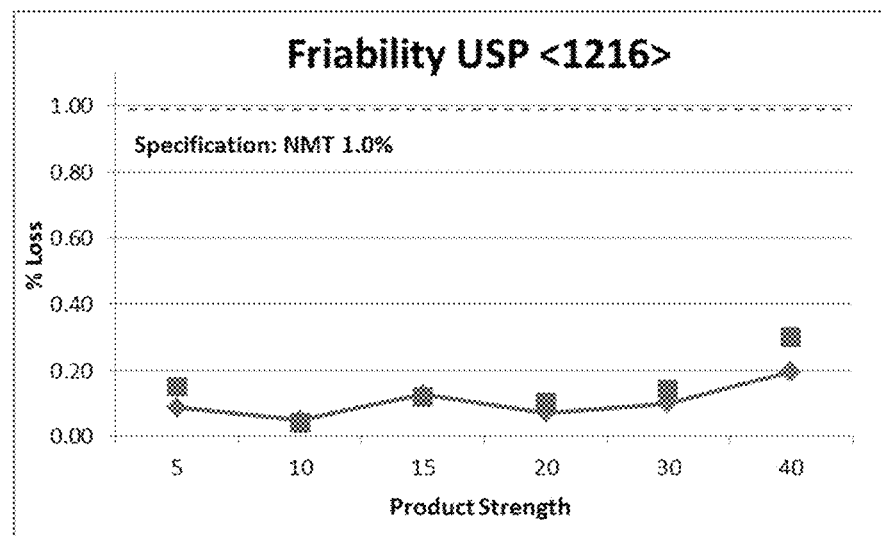
FIG. 8 shows the tablet friability as a function of compression force used to compress tablets of the registration stability batches when tested for friability by USP Method <2016>.
Figure 9:
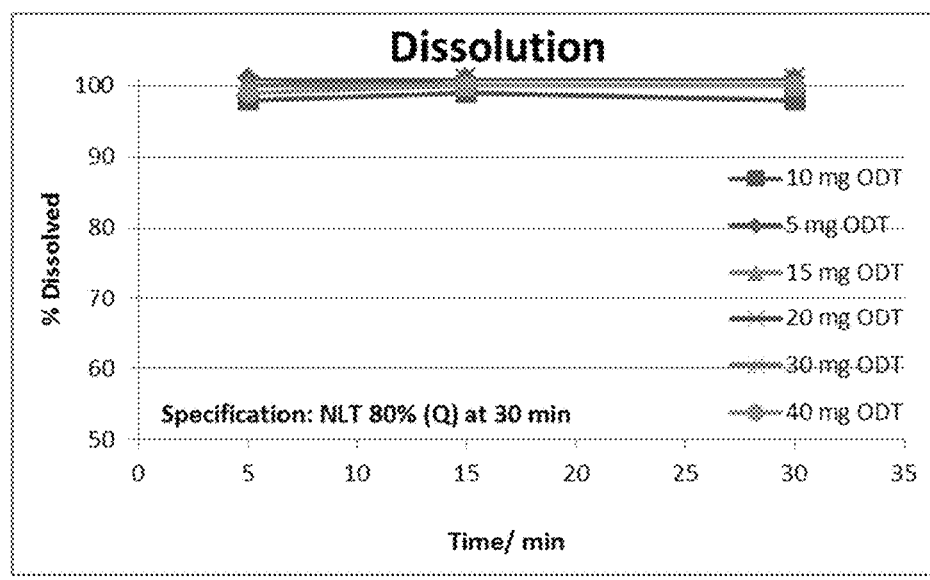
FIG. 9 shows the dissolution as a function of compression force used to compress tablets of the registration stability batches when tested for dissolution by USP Method <711>.

*Intended to be starting points for compression. Parameters may be adjusted, as needed, to produce tablets meeting the designated tablet attributes
For information only The composite tablets were release tested using the analytical test methods validated under QA-approved protocols. FIG. 5 shows the disintegration time as a function of compression force used to compress tablets of the registration stability batches. FIG. 6 shows the weight variation as a function of compression force used to compress tablets of the registration stability batches. FIG. 7 shows the tablet hardness as a function of compression force used to compress tablets of the registration stability batches. FIG. 8 shows the tablet friability as a function of compression force used to compress tablets of the registration stability batches when tested for friability by USP Method <2016>. FIG. 9** shows the dissolution as a function of compression force used to compress tablets of the registration stability batches when tested for dissolution by USP Method <711>.

Pivotal Bioequivalence Study: Amphetamine Sulfate IR ODTs vs RLD (EVEKEO®)

A pivotal, single-dose, open-label, three-period, three-treatment, six-sequence, crossover study was conducted in 42 healthy male or female adults aged 18-45 years was scheduled wherein each subject received a single dose of Amphetamine Sulfate on. Each drug administration followed an overnight fast of at least 10 hours. There was a washout period of at least 6 days between each dose. The primary objective of this pivotal study was to compare the bioavailability of amphetamine from Amphetamine Sulfate IR ODTs (test tablets) given as a single intact 20 mg tablet (1) swallowed with water (Treatment A), (2) given without water (Treatment B allowed the ODT to disintegrate on contact with saliva in the oral cavity and then swallow without water) and (3) Amphetamine Sulfate IR RLD (EVEKEO®) given as two intact 10 mg tablets swallowed with water (Reference or Treatment C), all under fasting condition. Each treatment was compared with each other.

Data were analyzed by non-compartmental methods in Phoenix™ WinNonlin® (Version 6.4, Pharsight Corporation). The following pharmacokinetic parameters were calculated: peak concentration in plasma ($C_{max}$), time to peak concentration ($T_{max}$), the time prior to the first quantifiable (non-zero) concentration ($T_{lag}$), elimination rate constant, terminal half-life ($t_{1/2}$), area under the concentration-time curve from time-zero to the time of the last quantifiable concentration ($AUC_{last}$), area under the plasma concentration time curve from time-zero extrapolated to infinity ($AUC_{inf}$), oral clearance (CL/F) for racemic amphetamine only, and oral volume of distribution (Vz/F) for racemic amphetamine only. The pharmacokinetic parameters of d-amphetamine and l-amphetamine (primary analysis) and racemic amphetamine (d-amphetamine plus l-amphetamine) (secondary analysis) were listed in tables of individual values and aggregated in summary tables by analyte using the following descriptive statistics: N, mean, standard deviation (SD), coefficient of variation (CV %), minimum, maximum, and median.

Overall, the study medications were generally well-tolerated by subjects in this study. Table 13 shows the PK Parameters (Mean±S.D.) observed in the pivotal bioequivalence study in healthy volunteers wherein 20 mg Amphetamine sulfate IR ODTs dosed with and without water vs. 2×10 mg (20 mg) dosed with water. Both Treatment A and B wherein the Amphetamine Sulfate IR ODTs, 20 mg test tablets orally administered with and without water were bioequivalent to the RLD EVEKEO® given as two intact 10 mg Amphetamine sulfate IR tablets swallowed with water.

TABLE 13

PK Parameters (Mean ± S.D.) for d,l-amphetamine sulfate observed in the pivotal bioequivalence study

| PK Parameter | n= | $T_{max}$ (hrs) | $C_{max}$ (ng/mL) | $AUC_{inf}$ (hr * ng/mL) | 90% Conf. Interval Lower | Upper |
|---|---|---|---|---|---|---|
| Treatment A | 39 | 2.74 ± 0.909 | 29.9 ± 5.28 | 506 ± 98.6 | ~97/98 | ~102/105 |
| Treatment B | 40 | 3.28 ± 0.698 | 29.4 ± 5.94 | 506 ± 107 | ~97/98 | ~102/104 |
| Treatment C | 39 | 2.51 ± 0.934 | 29.4 ± 4.93 | 493 ± 85.8 |  |  |

What is claimed is:

1. An orally disintegrating pharmaceutical composition comprising:
   (a) taste-masked drug containing particles comprising:
      (i) drug-containing core particles comprising a therapeutically effective amount of racemic amphetamine, or a pharmaceutically acceptable salt or ester thereof and at least one excipient;
      (ii) a first taste-masking membrane comprising ethylcellulose and excluding pharmaceutically acceptable gastrosoluble polymers, wherein the first taste-masking membrane is disposed on the drug-containing core particles and has a membrane thickness of from about 5% to about 10% by wt. of the taste-masked drug containing particle, and
      (iii) a second taste-masking membrane comprising ethylcellulose and aminoalkyl methacrylate copolymer at a ratio of about 50/50 by wt., wherein the second taste-masking membrane is disposed on the first taste-masking membrane and the second taste-masking membranes has a thickness of from about 15% to about 30% by wt. of the taste-masked drug containing particle;

(b) a disintegrant;

(c) a sugar alcohol or saccharide, or mixture thereof; and wherein if the orally disintegrating pharmaceutical composition comprises 30 mg of racemic amphetamine sulfate, after administration the orally disintegrating pharmaceutical composition provides one or more of the following:

an $AUC_{inf}$ ranging from about 80% to about 125% of about 400-600 hr*ng/mL;

a $C_{max}$ ranging from about 80% to about 125% of about 25-35 ng/mL; or a $T_{max}$ ranging from about 80% to about 125% of about 2-4 hrs.

2. The orally disintegrating pharmaceutical composition of claim 1, wherein the therapeutically effective amount of racemic amphetamine, or a pharmaceutically acceptable salt or ester thereof in the drug containing core particles is a dose equivalent to 30 mg of racemic amphetamine sulfate, wherein after administration, the orally disintegrating pharmaceutical composition provides two or more of the following:

an $AUC_{inf}$ ranging from about 80% to about 125% of about 400-600 hr*ng/mL;

a $C_{max}$ ranging from about 80% to about 125% of about 25-35 ng/mL; or a $T_{max}$ ranging from about 80% to about 125% of about 2-4 hrs.

3. The orally disintegrating pharmaceutical composition of claim 1, wherein the therapeutically effective amount of racemic amphetamine, or a pharmaceutically acceptable salt or ester thereof in the drug containing core particles is a dose equivalent to 30 mg of racemic amphetamine sulfate, wherein after administration, the orally disintegrating pharmaceutical composition provides the following:

an $AUC_{inf}$ ranging from about 80% to about 125% of about 400-600 hr*ng/mL;

a $C_{max}$ ranging from about 80% to about 125% of about 25-35 ng/mL; and a $T_{max}$ ranging from about 80% to about 125% of about 2-4 hrs.

4. The orally disintegrating pharmaceutical composition of claim 1, wherein the ethylcellulose in the first taste-masking membrane has a viscosity of about 100 cps.

5. The orally disintegrating pharmaceutical composition of claim 1, wherein the ethylcellulose in the second taste-masking membrane has a viscosity of about 10 cps.

6. The orally disintegrating pharmaceutical composition of claim 1, wherein the ethylcellulose in the first taste-masking membrane has a viscosity of about 100 cps, and the ethylcellulose in the second taste-masking membrane has a viscosity of about 10 cps.

7. The orally disintegrating pharmaceutical composition of claim 1, wherein the disintegrant and the sugar alcohol and/or saccharide are present together in the form of rapidly dispersing microgranules.

8. The orally disintegrating pharmaceutical composition of claim 7, wherein the rapidly dispersing microgranules have an average particle size of not more than about 300 μm.

9. The orally disintegrating pharmaceutical composition of claim 8, wherein the disintegrant has an average particle diameter of not more than about 30 μm.

10. The orally disintegrating pharmaceutical composition of claim 8, wherein the sugar alcohol and/or saccharide has an average particle diameter of not more than about 30 μm.

11. The orally disintegrating pharmaceutical composition of claim 1, wherein taste-masked drug containing particles have an average particle size of not more than about 400 μm.

12. The orally disintegrating pharmaceutical composition of claim 1, wherein the excipient in the drug-containing core particles is mannitol, the racemic amphetamine, or a pharmaceutically acceptable salt or ester thereof is racemic amphetamine sulfate, and the drug-containing core particles are an amphetamine sulfate-mannitol granulate.

13. The orally disintegrating pharmaceutical composition of claim 1, wherein the excipient in the drug-containing core particle is a bead, the racemic amphetamine, or a pharmaceutically acceptable salt or ester thereof is racemic amphetamine sulfate, and the drug-containing core particles are an amphetamine sulfate layered bead.

14. The orally disintegrating pharmaceutical composition of claim 1, wherein the therapeutically effective amount of racemic amphetamine, or a pharmaceutically acceptable salt or ester thereof is a dose equivalent to about 30 mg.

15. The orally disintegrating pharmaceutical composition of claim 1, wherein the therapeutically effective amount of racemic amphetamine, or a pharmaceutically acceptable salt or ester thereof in the drug containing core particles is in the range of from about 5 mg to about 40 mg.

16. The orally disintegrating pharmaceutical composition of claim 15, wherein the therapeutically effective amount of racemic amphetamine, or a pharmaceutically acceptable salt or ester thereof in the drug containing core particles is a dose equivalent to about 5 mg of racemic amphetamine sulfate.

17. The orally disintegrating pharmaceutical composition of claim 15, wherein the therapeutically effective amount of racemic amphetamine, or a pharmaceutically acceptable salt or ester thereof in the drug containing core particles is a dose equivalent to about 10 mg of racemic amphetamine sulfate.

18. The orally disintegrating pharmaceutical composition of claim 15, wherein the therapeutically effective amount of racemic amphetamine, or a pharmaceutically acceptable salt or ester thereof in the drug containing core particles is a dose equivalent to about 15 mg of racemic amphetamine sulfate.

19. The orally disintegrating pharmaceutical composition of claim 15, wherein the therapeutically effective amount of racemic amphetamine, or a pharmaceutically acceptable salt or ester thereof in the drug containing core particles is a dose equivalent to about 20 mg of racemic amphetamine sulfate.

20. The orally disintegrating pharmaceutical composition of claim 15, wherein the therapeutically effective amount of racemic amphetamine, or a pharmaceutically acceptable salt or ester thereof in the drug containing core particles is a dose equivalent to about 25 mg of racemic amphetamine sulfate.

21. The orally disintegrating pharmaceutical composition of claim 15, wherein the therapeutically effective amount of racemic amphetamine, or a pharmaceutically acceptable salt or ester thereof in the drug containing core particles is a dose equivalent to about 30 mg of racemic amphetamine sulfate.

22. The orally disintegrating pharmaceutical composition of claim 15, wherein the therapeutically effective amount of racemic amphetamine, or a pharmaceutically acceptable salt or ester thereof in the drug containing core particles is a dose equivalent to about 40 mg of racemic amphetamine sulfate.

* * * * *